(12) United States Patent
Marriott

(10) Patent No.: US 7,301,020 B2
(45) Date of Patent: Nov. 27, 2007

(54) MACROLIDE ANALOGS AND METHODS FOR IDENTIFYING SAME

(75) Inventor: Gerard Marriott, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 200 days.

(21) Appl. No.: 10/710,069

(22) Filed: Jun. 16, 2004

(65) Prior Publication Data

US 2004/0259185 A1 Dec. 23, 2004

Related U.S. Application Data

(60) Provisional application No. 60/479,770, filed on Jun. 19, 2003.

(51) Int. Cl.
*C07D 267/22* (2006.01)
(52) U.S. Cl. ..................................... 540/469
(58) Field of Classification Search ................. 514/375; 540/469
See application file for complete search history.

(56) References Cited

U.S. PATENT DOCUMENTS

| | | | | |
|---|---|---|---|---|
| 5,260,224 | A | 11/1993 | Stossel | 436/503 |
| 5,508,265 | A | 4/1996 | Stossel | 514/12 |
| 5,691,160 | A | 11/1997 | Janmey | 435/13 |
| 5,985,608 | A | 11/1999 | Luna | 435/69.1 |
| 6,312,926 | B1 | 11/2001 | Shatkin | 435/349 |
| 2002/0103112 | A1 | 8/2002 | Ferguson | 514/2 |

OTHER PUBLICATIONS

Bubb, M.R., et al., "Swinholide A is a microfilament disrupting marine toxin that stabilizes actin dimers and severs actin filaments," J Biol Chem. Feb. 24;270(8):3463-6 (1995).
D'Auria, M.V., Paloma, L.G. "Reidispongiolide A and B, Two new potent cytotoxic macrolides from the New Caladonian Sponge." Tetrahedron 50(16): 4829-4834 (1994).
Guella, G., et al. "Sphinxolide, a 26-Membered Antitumoral Macrolide isolated from an unidentified Pacific Nudibranch." Helvetica Chimica Acta, 72 :237-246 (1994).
Ishibashi, M., Moore, R.E., Patterson, G. "Scytophycins, Cytotoxic and antimoycotic agents from the cyanophyte Scytonema pseudohofmanni." J. Org. Chem., 51:5300-5306 (1986).
Jefford, C.W. , Bernardinelli, G., "Structures and absolute configurations of the marine toxins Latrunculin A and Laulimalide." Tetrahedron Letters, 37(2):159-162 (1996).
Kobayashi M, Tanaka J, Katori T, Kitagawa I. "Marine natural products. XXIII. Three new cytotoxic dimeric macrolides, swinholides B and C and isoswinholide A, congeners of swinholide A, from the Okinawan marine sponge *Theonella swinhoei*." Chem Pharm Bull (Tokyo), Nov. 38(11):2960-6 (1996).
Marriott G, Zechel K, Jovin TM. "Spectroscopic and functional characterization of an environmentally sensitive fluorescent actin conjugate." Biochemistry, 27(17):6214-20 (Aug. 23, 1996).
Marriott G, Miyata H, Kinosita K Jr. "Photomodulation of the nucleating activity of a photocleavable crosslinked actin dimer." Biochem Int. 26(5):943-51 (Apr. 1992).
Matsunaga, S., et al. "Kabiramide C, a novel antifungal Macrolide from Nuidibranch Eggmasses." J. Am. Chem. Soc. 108:847-849 (1986).
Morton W.M., et al."Latrunculin alters the actin-monomer subunit interface to prevent polymerization." Nat Cell Biol.2(6):376-8 (Jun. 2000).
Roesener, J.A., Scheuer, P.J. "Ulapualide A and B, Extraordinary antitumor macrolides from Nudibranch eggmasses." J. Am. Chem. Soc. 108: 846-847 (1986).
Saito, S., Karaki, H. "A family of novel actin-inhibiting marine toxins." Clinical and Experimental Pharmacology and Physiology, 23:743-746 (1996).
Tanaka, J., et al. "Marine Natural Products. XXIV The absolute stereostructure of misakinolide A a potent cytotoxic dineric macrolide from an Okinawan marine sponge *Theonella* sp." Chem. Pharm. Bull. 38(11): 2967-2970 (1990).
Terry D.R, Spector I, Higa T, Bubb M.R. "Misakinolide A is a marine macrolide that caps but does not sever filamentous actin." J Biol Chem.272(12):7841-5 (Mar. 21, 1997).
Wada S, et al.. "Actin-binding specificity of marine macrolide toxins, mycalolide B and kabiramide D." J Biochem (Tokyo). 123(5):946-52 (May 1998).
Yamada, K, et al. "Aplyronine A, a potent antitumor substance, and the congeners aplyronines B and C isolated from the sea hare aplysia kurodai." J. Am. Chem. Soc. 115:11020-11021 (1993).
Zechel K. "The interaction of 6-propionyl-2-(NN-dimethyl)aminonaphthalene (PRODAN)-labelled actin with actin-binding proteins and drugs." Biochem J., 290 (Pt 2):411-7 (Mar. 1, 1993).

*Primary Examiner*—Elli Peselev
(74) *Attorney, Agent, or Firm*—Quarles & Brady LLP

(57) ABSTRACT

Macrolide analogs and methods for identifying macrolide analogs capable of unregulated inhibition of actin filament dynamics are provided. A method according to the invention includes the steps of: (a) contacting F-actin with a candidate compound; and (b) assaying the candidate compound's ability to sever the F-actin and cap resulting F-actin (+)-ends. The candidate compound is identified as a macrolide analog where said candidate compound displays an ability to sever F-actin and, following severing, the resulting F-actin (+)-end is capped by the candidate compound thusly preventing subsequent G-actin incorporation. Severing and capping activities are unregulated; i.e., independent of at least physiologically-meaningful concentrations of phosphatidyl inositol and calcium.

1 Claim, 9 Drawing Sheets

| | $R_1$ | $R_2$ | $R_3$ | $R_4$ | $R_5$ | $R_6$ | $R_7$ | $R_8$ | Δ |
|---|---|---|---|---|---|---|---|---|---|
| Kabiramide C | CONH$_2$ | Me | OH | Me | α-OMe | OMe | Me | Me | |
| Jaspisamide A | H | OH | O | Me | β-OMe | H | Me | H | |
| Mycalolide A | H | H | O | Me | β-OMe | OMe | Ac | Me | 5,6 |
| Ulapualide A | H | H | O | H | OMe | OMe | Ac | Me | |
| Halichondramide | H | H | O | Me | β-OMe | H | Me | H | 5,6 |
| Halishigamide A | H | NH$_2$ | O | Me | β-OMe | H | Me | H | |

*A:* *KabC binds to G-actin forming a very stable complex*

*B:* *G-Actin-KabC caps actin filament (+)-ends*

*C:* *KabC severs actin filaments and caps the (+)-end*

MACROLIDE ANALOGS AND METHODS FOR IDENTIFYING SAME

CROSS REFERENCE TO A RELATED APPLICATION

The present application seeks priority from U.S. Provisional Application No. 60/479,770, filed on Jun. 19, 2003, which is incorporated by reference in its entirety.

TECHNICAL FIELD

This invention relates generally to inhibitors of actin filament dynamics useful in treating actin-related diseases or injuries. In particular, this invention is directed to macrolide analogs and methods for identifying macrolide analogs capable of unregulated inhibition of actin filament dynamics.

BACKGROUND ART

The assembly of actin filaments represents a dynamic biological process essential for an organism's survival. For example, actin filament dynamics provide the foundation for cellular motility necessary in the wound healing response and the neutralization of bacteria by neutrophils (Bamburg and Wiggin, 2002; Asch et al, 1996). Actin filament dynamics have further been identified as playing a key role in various pathologies including tumor metastasis, cystic fibrosis, organ infarction and glaucoma. It can be appreciated that, with the ever-increasing understanding of actin's integral role in disease and injury, there is a growing interest in identifying new and improved actin-targeted therapeutics.

Marine organisms, especially soft corals, sponges and tunicates, provide many secondary metabolites including the macrolides which are known to be cytotoxic through inhibition of actin filament dynamics (Saito et al, 1994; Wada et al, 1998; Bubb et al, 1995; Spector et al, 2002). These drugs can be classified as: (1), macrolides that contain a trisoxazole group and are typified by Kabiramide C (KabC; Matsunaga et al, 1986; Wada et al, 1998; FIG. 1A) and Ulapualide A (UlaA; FIG. 1A-C; Roesener and Scheuer, 1986); and (2), dimeric macrolides such as Swinholide A (SwiA; Bubb et al, 1995; Saito et al, 1996). A review of the chemical database details more than 30 different members within these macrolide families. Certain members of the trisoxazole macrolide family may act as actin monomer sequestering and severing drugs (Saito et al, 1996; Wada et al, 1998), while SwiA is thought to sequester actin dimers during the nucleation phase of filament growth (Bubb et al, 1995), and misakinolide A (MisA; Terry et al, 1997) is purported to bind to the actin dimer at the (+)-end of the filament where it blocks further growth. While understood to be effective in actin filament inhibition, the detailed molecular mechanism of how these natural products interact with actin was unknown before the inventor's present efforts, reported herein. Without this knowledge, the identification and rational design of macrolide functional derivatives could not be reliably carried out by those working in the field.

Based upon a need in the field, it is desirable to obtain additional macrolide analogs capable of, most preferably, unregulated F-actin (+)-end capping, F-actin severing and G actin monomer sequestration. The unregulated activity of such analogs would be in contrast to the regulated actin-capping proteins currently known such as gelsolin, CapG and Capping Protein (reviewed by Cooper and Schafer, 2000). The therapeutic use of these respective actin-capping proteins is hampered by their responsiveness to physiological cues such as second messengers including calcium and phosphatidyl inositol (e.g., PIP and $PIP_2$). Additional macrolide analogs would find use in, for example, the treatment of actin-containing clots, viscous mucus in cystic fibrosis, glaucoma, tumor growth and/or as a substitute for plasma gelsolin in patients suffering burns and trauma. Methods for screening and identifying new macrolide analogs based upon the present inventor's recent elucidation of macrolide: actin interactions would be particularly desirable and a welcome advancement in the field.

SUMMARY OF THE INVENTION

The present invention provides a method for identifying macrolide analogs capable of unregulated inhibition of actin filament dynamics. In one embodiment, the method includes the steps of: (a) contacting F-actin with a candidate compound; and (b) assaying the candidate compound's ability to sever the F-actin and cap resulting F-actin (+)-ends. The candidate compound is identified as a macrolide analog where the candidate compound displays an ability to sever F-actin and, following severing, the resulting F-actin (+)-end is capped by the candidate compound thusly preventing subsequent G-actin incorporation. Furthermore, the severing and capping activities are independent of physiological cues including at least calcium and phosphatidyl inositol.

In one embodiment, the above-described method assays a candidate compound comprising: (a) a macrolide ring capable of binding F-actin at the entrance to the cleft between sub-domains 1 and 3; and (b) a hydrophobic tail capable of interacting with the cleft between sub-domains 1 and 3. The hydrophobic tail is capable of disrupting a bond between actin protomers with the hydrophobic tail subsequently remaining bound to the (+)-end protomer to cap the resulting F-actin (+)-end.

In another embodiment, the above-described method assays a candidate compound comprising: (a) a macrolide ring; and (b) a hydrophobic tail. In a preferred embodiment, the candidate compound being assayed is a tris (oxazole)-containing compound.

In another embodiment, the present invention is directed to a method for identifying a macrolide analog capable of unregulated inhibition of actin filament dynamics. The method includes the steps of: (a) determining an observed binding rate, $k_{obs}$, of a candidate compound to G-actin; (b) determining a dissociation constant of the candidate compound with G-actin; and (c) determining the candidate compound's ability to sever F-actin. The candidate compound is identified as a macrolide analog where: (i) the observed binding rate, $k_{obs}$, for the candidate compound to G-actin exhibits two binding steps, a first primary binding step having a rate of about 10 $s^{-1}$ to about 50 $s^{-1}$ and a secondary binding step having a rate of about 0.001 $s^{-1}$ to about 0.010 $s^{-1}$; (ii) a dissociation constant from G-actin of about 10 nM to about 150 nM; (iii) an ability to sever F-actin, said severing ability associated with the secondary binding step and, following severing, the resulting F-actin (+)-end is capped thusly preventing G-actin incorporation; and (iv) the severing and capping activities are independent of physiologically-meaningful concentrations of phosphatidyl inositol and calcium.

In yet another embodiment, the present invention provides a method for identifying a macrolide analog capable of unregulated inhibition of actin filament dynamics. The method includes the steps of: (a) determining an observed binding rate, $k_{obs}$, of a candidate compound to G-actin, said candidate compound including a macrolide ring and a hydrophobic tail; (b) determining a dissociation constant of the candidate compound with G-actin; and (c) determining the candidate compound's ability to sever F-actin. The candidate compound is identified as a macrolide analog where: (i) the observed binding rate, $k_{obs}$, for the candidate compound to G-actin exhibits two binding steps: (1) a first primary binding step having a rate of about 10 $s^{-1}$ to about 50 $s^{-1}$ associated with the macrolide ring binding G-actin; and (2) a secondary binding step having a rate of about 0.001 $s^{-1}$ to about 0.010 $s^{-1}$ associated with the hydrophobic tail binding G-actin; (ii) a dissociation constant from G-actin of about 10 nM to about 150 nM; (iii) an ability to sever F-actin, said severing ability associated with the secondary binding step and due at least in part to the disruption of an interaction between actin protomers by the hydrophobic tail and, following severing, the resulting F-actin (+)-end is capped thusly by the hydrophobic tail preventing G-actin incorporation; and (iv) the severing and capping activities are independent of physiologically-meaningful concentrations of phosphatidyl inositol and calcium.

The invention further encompasses analogs of kabiramide C comprising a modification at the 7'-hydroxyl position on the macrolide ring as identified by any one of the methods described above and claimed herein. In preferred embodiments, the analog is modified at the 7'-hydroxyl position on the macrolide ring with a methoxycourmarin (MC) or diethylaminocoumarin (DEAC) group.

In addition to methods of identifying particular molecules, the present invention also encompasses macrolide analogs useful for inhibiting actin filament dynamics. These analogs include: (a) a macrolide ring capable of binding F-actin at the entrance to the cleft between sub-domains 1 and 3 of said F-actin; and (b) a hydrophobic tail capable of interacting with the cleft between sub-domains 1 and 3. The hydrophobic tail is further capable of severing an interaction between actin protomers with the hydrophobic tail subsequently remaining bound to the (+)-end protomer to cap the resulting F-actin (+)-end.

In particular embodiments, the analog is further characterized by: (a) the macrolide ring binding F-actin in a first primary binding step having an observed binding rate of about 10 $s^{-1}$ to about 50 $s^{-1}$; and (b) the hydrophobic tail binding F-actin in a secondary binding step having a rate of about 0.001 $s^{-1}$ to about 0.010 $s^{-1}$. The analog preferably exhibits a dissociation constant from F-actin of about 10 nM to about 150 nM and, even more preferably, the severing and capping activities are independent of at least physiologically-meaningful concentrations of phosphatidyl inositol and calcium.

Certain preferred embodiments of macrolide analogs further include a targeting moiety coupled to the macrolide ring for directing an analog to a specific tissue or cell type. A particularly preferred embodiment is kabiramide C derivatized at the 7'-hydroxyl position with the targeting moiety.

Particular analogs according to the invention, while being generally useful for inhibiting actin filament dynamics, are additionally useful in detecting actin filaments. In preferred embodiments, these analogs include a tris (oxazole)-containing macrolide or functional derivative thereof wherein the 7'-hydroxyl position on the macrolide ring is modified with a fluorescent moiety. In certain embodiments, the fluorescent moiety is a methoxycourmarin (MC) or a diethylaminocoumarin (DEAC) group.

Macrolide analogs useful in detecting actin filaments, as described and claimed herein, facilitate microscopy methods for observing actin filaments wherein actin filaments are contacted with such analogs. Such microscopy methods are preferably carried out on actin filaments contained within living cells. Microscopy methods utilizing the macrolide analogs of the present invention are further envisioned to be offered in kit form.

Other objects, features and advantages of the present invention will become apparent after review of the specification, claims and drawings.

Cell death occurs in (D) within 8~12 hours. At 10~100 nM (B, C) the drug causes an increase in the number of blebs, a breakdown in the adherens junction and a cytokinesis defect as can be seen by the presence of 2-4 nuclei while control cells harbor a single nucleus. At 100 nM the cells lose control of contractile functions and have enlarged vesicles.

Figure 8:
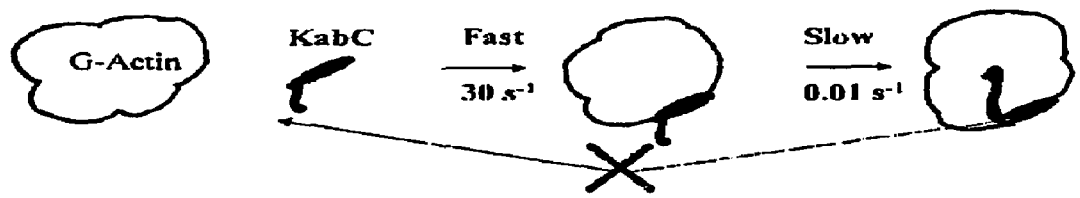
Figure 8:
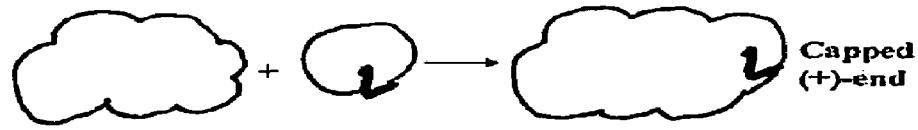
Figure 8:
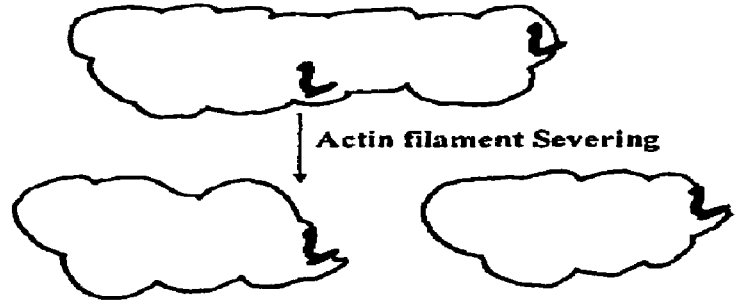

FIG. 8: Model to understand the mechanism of KabC inhibition of actin polymerization. A. Sequestering at stoichiometric concentrations of KabC to G-actin: The binding of KabC to G-actin is a 2-step reaction with a fast step involving the macrolide ring and a slow step involving the binding of the tail portion of the drug. The fully bound complex is extremely stable. B. (+)-end capping: The strongly bound KabC actin can incorporate onto the (+)-end of an actin filament but caps further filament growth. C. Filament Severing: KabC can bind to protomers in the filament where it competes for the cleft binding site between sub-domains 1/3 with the axial actin protomer. Once fully bound the filament severs and KabC caps the new (+)-end.

Figure 9:
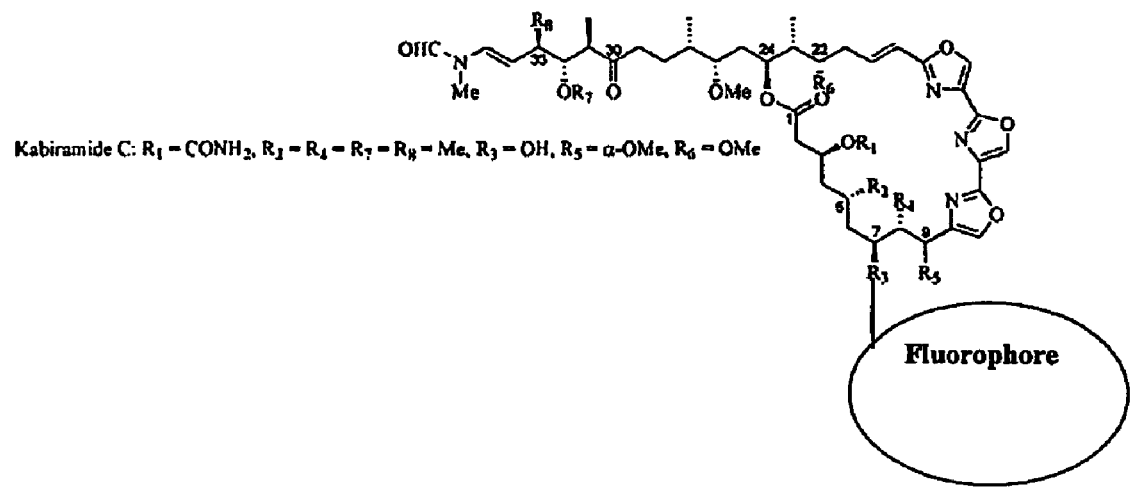

FIG. 9: Structure of kabiramide functional derivatives indicating the position of labeling at the 7'-hydroxyl group.

Figure 10:
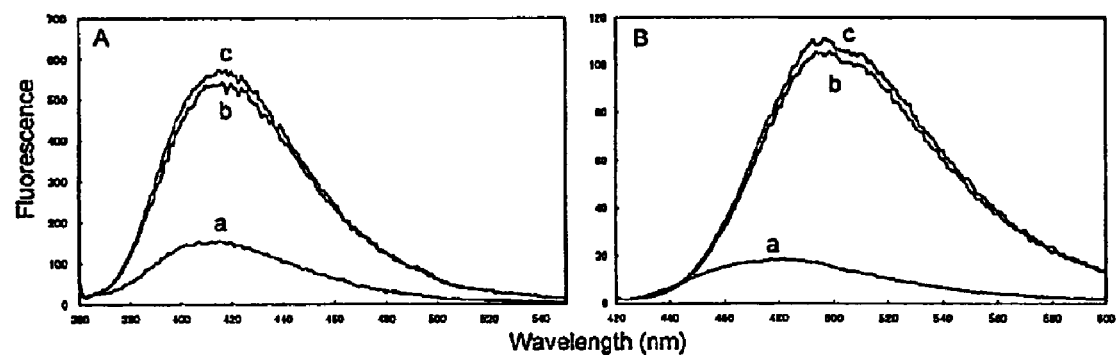

FIG. 10: Spectral and actin binding properties of new KabC functional derivatives useful as fluorescent probes. A), Emission spectra $\lambda$ex 345 nm of (i), MC-KabC in G-buffer; (ii), MC-KabC (i) with 5 $\mu$M G-actin; (iii), same sample as in (ii) but after 15 minutes. B), Emission spectra $\lambda$ex 390 nm of (i), DMAC-KabC in G-buffer; (ii), DMAC-KabC (i) with 5 $\mu$M G-actin; (iii), same sample as in (ii) but 15 minutes after adding 5 $\mu$M CapG.

Figure 11:
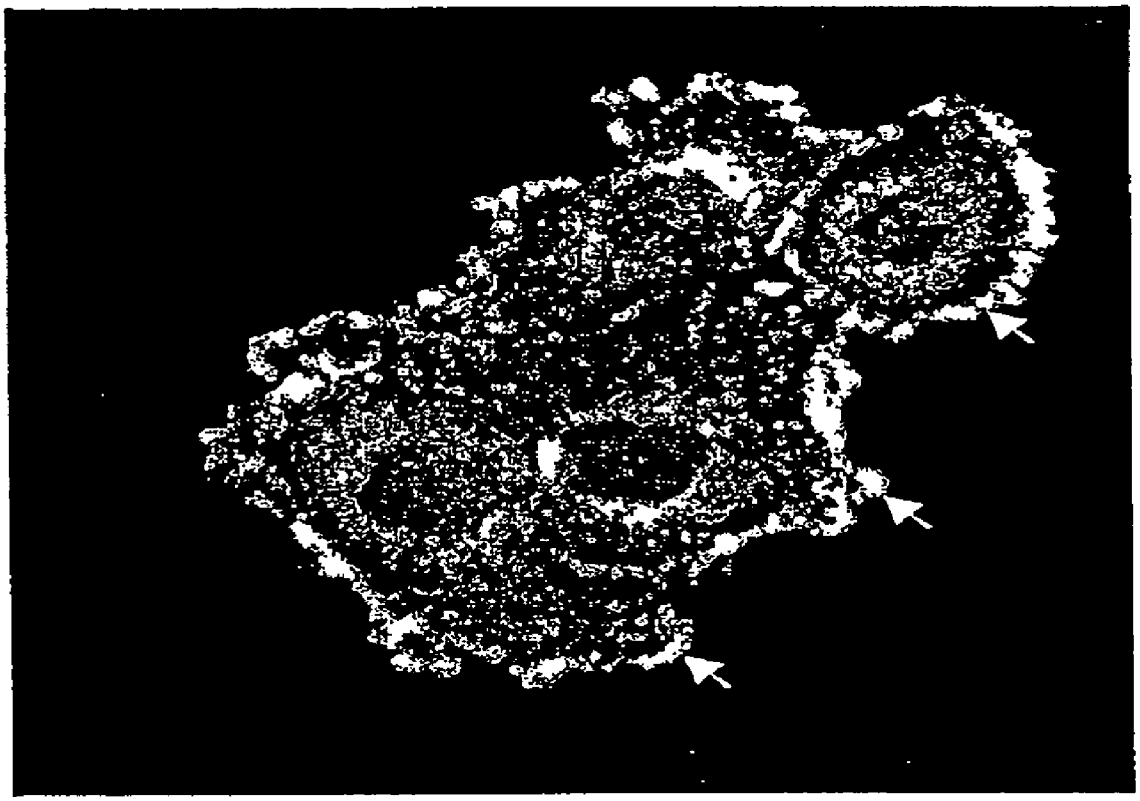

FIG. 11: Confocal fluouresence image of fluorescein-KabC in live NBT-II cells. The cells were labeled with a low concentration (not determined) of the fluorescein diester derivative of KabC. After 30 minutes the cells were imaged using 488 nm ex, 520 nm em. The confocal images were recorded in the Gomez laboratory at the University of Wisconsin-Madison. White arrows are sites of cell protrusion.

DISCLOSURE OF INVENTION

In General

Before the present methods are described, it is understood that this invention is not limited to the particular methodology, protocols, cell lines, and reagents described, as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural reference unless the context clearly dictates otherwise. Thus, for example, reference to "a cell" includes a plurality of such cells and equivalents thereof known to those skilled in the art, and so forth. As well, the terms "a" (or "an"), "one or more" and "at least one" can be used interchangeably herein. It is also to be noted that the terms "comprising", "including", "characterized by" and "having" can be used interchangeably.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference for the purpose of describing and disclosing the chemicals, cell lines, vectors, animals, instruments, statistical analysis and methodologies which are reported in the publications which might be used in connection with the invention. Nothing herein is to be construed as an admission that the invention is not entitled to antedate such disclosure by virtue of prior invention.

The practice of the present invention will employ, unless otherwise indicated, conventional techniques of molecular biology, microbiology, recombinant DNA, and immunology, which are within the skill of the art. Such techniques are explained fully in the literature. See, for example, Molecular Cloning A Laboratory Manual, 2nd Ed., ed. by Sambrook, Fritsch and Maniatis (Cold Spring Harbor Laboratory Press: 1989); DNA Cloning, Volumes I and II (D. N. Glover ed., 1985); Oligonucleotide Synthesis (M. J. Gait ed., 1984); Mullis et al. U.S. Pat. No. 4,683,195; Nucleic Acid Hybridization (B. D. Hames and S. J. Higgins eds. 1984); Transcription And Translation (B. D. Hames and S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the treatise, Methods In Enzymology (Academic Press, Inc., N.Y.); Gene Transfer Vectors For Mammalian Cells (J. H. Miller and M. P. Calos eds., 1987, Cold Spring Harbor Laboratory); Methods In Enzymology, Vols. 154 and 155 (Wu et al. eds.), Immunochemical Methods In Cell And Molecular Biology (Mayer and Walker, eds., Academic Press, London, 1987); Handbook Of Experimental Immunology, Volumes I-IV (D. M. Weir and C. C. Blackwell, eds., 1986).

In order to provide a clearer and consistent understanding of the specification and claims, including the scope to be given such terms, the following definitions are provided.

The "biological activity" of the macrolide analogs described and claimed herein is their ability to perform unregulated F-actin (+)-end capping, F-actin severing and G actin monomer sequestration comparable to a corresponding natural macrolide. The term "unregulated", as used herein to refer to the biological activity of the macrolide analog, shall mean the macrolide analogs are not responsive or are insensitive to physiological cues including, at least, Ca ion and phosphatidyl inositol (e.g., PIP and $PIP_2$) at physiologically-relevant levels otherwise known to be cues for Cap G, gelsolin and Capping Protein.

An "analog" of a macrolide is meant to refer to a non-naturally-occurring compound substantially similar in biological activity to a native (i.e., naturally-occurring) macrolide. For example, an analog of a macrolide is a molecule which does not have the same chemical structure but which is sufficiently homologous to a natural macrolide so as to retain the biological activity of a corresponding native macrolide. By "substantially similar" is meant biological activity which may differ quantitatively but is qualitatively the same. For example, an analog of a macrolide may contain the same conserved hydrophobic tail region and macrolide ring but also contain other modifications such as a chemical modification of a side chain (e.g., the 7'-hydroxyl group of the macrolide ring, described below) while retaining substantially similar biological activity to the corresponding natural macrolide. Such analogs may improve the compound's solubility, absorption, biological half life, or specificity for a target tissue or cell type, etc. The analogs may also decrease the toxicity of the molecule, or eliminate or attenuate any undesirable side effect of the molecule, etc. Exemplary chemical moieties capable of mediating such effects are disclosed in Remington's Pharmaceutical Sciences (1980). Procedures for coupling such moieties to a molecule are well known in the art. The term "analog" is intended to include the terms "variants," and "functional derivatives." As defined herein, "analog" shall also encompass mimetics of macrolides.

A "variant" of a macrolide is meant to refer to a non-naturally-occurring compound substantially similar in structure and biological activity to the corresponding native macrolide. A "functional derivative" of a macrolide is meant to refer to a non-naturally-occurring compound substantially similar in structure and biological activity to a native macrolide compound and derived from the native macrolide by, for example, chemical modification of the native macrolide to obtain a modified, non-naturally-occurring molecule. "Non-naturally-occurring" shall mean the analog, variant or functional derivative does not occur in nature, therefore excluding isolated and purified natural products.

As used herein, "physiological cues" refers to physiologically relevant concentrations of effectors including at least the second messengers calcium or phosphatidyl inositol (e.g., $PIP_2$ and PIP), to which certain proteins and compounds are known to be responsive (e.g., gelsolin).

A "candidate compound" refers to any molecule assayable by the methods described herein. Preferably, a candidate compound comprises at least a macrolide ring and a hydrophobic tail and is a chemical derivative, analog, fragment, or variant of a naturally-occurring macrolide. Candidate compounds may be generated by techniques known in the art including, but not limited to, de novo chemical synthesis, chemical derivatization of naturally-occurring macrolides, in vivo or in vitro biosynthesis using recombinantly-expressed enzymes including enzymes responsible for macrolide biosynthesis, or any combination thereof. It certainly envisioned that candidate compounds may be generated using combinatorial approaches, both chemical and recombinant DNA-based, well known in the art so as to generate a chemical library to be assayed by the methods of the present invention. Such screening may further be automated by known techniques to speed screening of combinatorial libraries. As well, new salts of macrolides may be made by adding mineral acids, e.g., HCl, $H_2SO_4$, etc. or strong organic acids, e.g., formic, oxalic, etc., in appropriate amounts to form the acid addition salt of the parent macrolide or derivative. Standard chemical reactions useful in preparing candidate compounds include the commonly known reactions of hydrogenation, methylation, acetylation and acidification reactions. Two examples of addition products are described in the Examples section below, assayed by the present methods, and thusly identified as macrolide analogs.

When an analog or other molecule "displays an ability" or "is capable of" a certain activity or "interacts" in a particular manner, such actions or attributes are meant to be present and demonstratable at statistically significant levels as demonstrated by statistical analysis techniques accepted in the field (e.g., the Student's t-Test).

"Dissociation constant" and "observed binding rate" shall be defined and their values determined as described in the Materials and Methods section below and in the particular references cited therein. In addition, all values related to thermodynamics, stoichiometry, dissociation constants, binding rates, polymerization, and depolymerization as discussed herein shall be arrived at according to the calculations described in the Materials and Methods section below. Values from references outside this disclosure must therefore be expressed in similar units and have been collected under or equated using substantially similar variables such as time, temperature, concentration and pressure before meaningful comparison may be carried out. One skilled in the art may calculate and manipulate thermodynamic values through commonly known mathematical algorithms.

The term "macrolide ring" shall refer to the general cyclized ring structure present in known natural macrolides and analogs thereof. In terms of the methods and compositions described and claimed herein, a "macrolide ring" shall bind F-actin at the entrance to the cleft between sub-domains 1 and 3, as detailed in the Examples section below. As well, "hydrophobic tail" shall refer to the highly-conserved, substituted alkyl chain attached to and extending from the macrolide ring and analogs thereof. In terms of the methods and compositions described and claimed herein, a "hydrophobic tail" shall be at least capable of interacting with the cleft between sub-domains 1 and 3, preferably disrupting an interaction between actin protomers (i.e., severing), and most preferably remaining bound to the (+)-end protomer following severing to prevent interactions with actin monomers (i.e., capping).

The Invention

The present invention provides a method for identifying macrolide analogs capable of unregulated inhibition of actin filament dynamics. The method includes the steps of: (a) contacting F-actin with a candidate compound; and (b) assaying the candidate compound's ability to sever the F-actin and cap resulting F-actin (+)-ends. The candidate compound is identified as a macrolide analog where said candidate compound displays an ability to sever F-actin and, following severing, the resulting F-actin (+)-end is capped by the candidate compound thusly preventing subsequent G-actin incorporation. Furthermore, the severing and capping activities are independent of at least physiologically-meaningful concentrations of phosphatidyl inositol and calcium.

In one embodiment, the above-described method assays a candidate compound comprising: (a) a macrolide ring capable of binding F-actin at the entrance to the cleft between sub-domains 1 and 3; and (b) a hydrophobic tail capable of interacting with the cleft between sub-domains 1 and 3. The hydrophobic tail is capable of disrupting an interaction between actin protomers with the hydrophobic tail subsequently remaining bound to the (+)-end protomer to cap the resulting F-actin (+)-end.

In another embodiment, the above-described method assays a candidate compound comprising: (a) a macrolide ring; and (b) a hydrophobic tail. In a preferred embodiment, the candidate compound being assayed is a tris (oxazole)-containing compound.

The determination of binding stoichiometry, dissociation constants, and binding rates may be carried by readily available and well documented techniques known in the art. In preferred embodiments, these determinations are performed by the methods described in the following Examples section. In brief, the change in the quantum yield and/or emission energy of optical probes attached to the thiol group on Cys374 of actin can provide key information on molecular complexes of actin with macrolides and analogs thereof. Pyrene-actin (Kouyama and Mihashi, 1981; Cooper et al., 1983 and Prodan-actin (Marriott et al., 1988) are the best characterized fluorescent actin conjugates. Binding stoichiometry, dissociation constants, and binding rates are preferably determined using Prodan-actin assays, described below, although pyrene-actin or equivalent approaches may certainly be utilized by one of skill in the art to arrive at the various binding stoichiometry, dissociation constants, and binding rates described herein and recited in the appended claims.

In another embodiment, the present invention is directed to a method for identifying a macrolide analog capable of unregulated inhibition of actin filament dynamics. The method includes the steps of: (a) determining an observed binding rate, $k_{obs}$, of a candidate compound to G-actin; (b) determining a dissociation constant of the candidate compound with G-actin; and (c) determining the candidate compound's ability to sever F-actin. The candidate compound is identified as a macrolide analog where: (i) the observed binding rate, $k_{obs}$, for the candidate compound to G-actin exhibits two binding steps, a first primary binding step having a rate of about 10 to about 50 $s^{-1}$ and a secondary binding step having a rate of about 0.001 $s^{-1}$ to about 0.010 $s^{-1}$; (ii) a dissociation constant from G-actin of about 10 nM to about 150 nM; (iii) an ability to sever F-actin, said severing ability associated with the secondary binding step and, following severing, the resulting F-actin (+)-end is capped thusly preventing G-actin incorporation; and (iv) the severing and capping activities are independent of physiological cues, including physiologically-meaningful concentrations of phosphatidyl inositol and calcium.

In yet another embodiment, the present invention provides a method for identifying a macrolide analog capable of unregulated inhibition of actin filament dynamics. The method includes the steps of: (a) determining an observed binding rate, $k_{obs}$, of a candidate compound to G-actin, said candidate compound including a macrolide ring and a hydrophobic tail; (b) determining a dissociation constant of the candidate compound with G-actin; and (c) determining the candidate compound's ability to sever F-actin. The candidate compound is identified as a macrolide analog where: (i) the observed binding rate, $k_{obs}$, for the candidate compound to G-actin exhibits two binding steps: (1) a first primary binding step having a rate of about 10 $s^{-1}$ to about 50 $s^{-1}$ associated with the macrolide ring binding G-actin; and (2) a secondary binding step having a rate of about 0.001 $s^{-1}$ to about 0.010 $s^{-1}$ associated with the hydrophobic tail binding G-actin; (ii) a dissociation constant from G-actin of about 10 nM to about 150 nM; (iii) an ability to sever F-actin, said severing ability associated with the secondary binding step and due at least in part to the disruption of an interaction between actin protomers by the hydrophobic tail and, following severing, the resulting F-actin (+)-end is capped thusly by the hydrophobic tail preventing G-actin incorporation; and (iv) the severing and capping activities are independent of physiological cues, including physiologically-meaningful concentrations of phosphatidyl inositol and calcium.

The invention further encompasses analogs of kabiramide C comprising a modification at the 7'-hydroxyl position on the macrolide ring as identified by any one of the method described above and claimed herein. In preferred embodiments, the analog is modified at the 7'-hydroxyl position on the macrolide ring with a methoxycourmarin (MC) or diethylaminocoumarin (DEAC) group. These particular analogs, while finding use as actin filament dynamic inhibitors, are also advantageous as molecular probes due to their fluorescent nature. The compounds' utility may be most fully appreciated by review of the Examples section below.

An analog may be a mimetic structurally similar to a naturally-occurring macrolide, such that the mimetic possesses a biological activity that is substantially similar to the biological activity of the comparable natural macrolide. In general, "mimetics" are defined as organic compounds that mimic the three-dimensional shape and activity of a particular molecule. It is now accepted that mimetics may be designed based on techniques that evaluate three dimensional shape, such as nuclear magnetic resonance (NMR) and computational techniques. NMR is widely used for structural analysis of molecules. Cross-peak intensities in Nuclear Overhauser Enhancement (NOE) spectra, coupling constants and chemical shifts depend on the conformation of a compound. NOE data provide the inter-proton distance between protons through space. This information may be used to facilitate calculation of the lowest energy conformation for the relevant macrolide structure. Once the lowest energy conformation is known, the three-dimensional shape to be mimicked is known.

The analogs identified by the methods described herein are useful in treating conditions remediable by inhibition of actin filament dynamics include, but are not limited to, tumor growth, wound scarring, thrombosis, pneumonia, trauma, organ infarction, familial hypertrophic cardiomyopathy, apoptosis, abnormal neuron axonal growth, Wiskott-Aldrich disease, Nemaline myopathy, Finnish familial amyloidosis, bacterial infections, viral infections, cystic fibrosis or glaucoma.

In addition to methods of identifying macrolide analogs, the present invention further encompasses macrolide analogs useful for inhibiting actin filament dynamics. Such analogs include: (a) a macrolide ring capable of binding F-actin at the entrance to the cleft between sub-domains 1 and 3 of said F-actin; and (b) a hydrophobic tail capable of interacting with the cleft between sub-domains 1 and 3. The hydrophobic tail is further capable of severing an interaction between actin protomers with the hydrophobic tail subsequently remaining bound to the (+)-end protomer to cap the resulting F-actin (+)-end.

In particular embodiments, the analog is further characterized by: (a) the macrolide ring binding F-actin in a first primary binding step having an observed binding rate of about 10 $s^{-1}$ to about 50 $s^{-1}$; and (b) the hydrophobic tail binding F-actin in a secondary binding step having a rate of about 0.001 $s^{-1}$ to about 0.010 $s^{-1}$. The analog preferably exhibits a dissociation constant from F-actin of about 10 nM to about 150 nM and, even more preferably, the severing and capping activities are independent of at least physiologically-meaningful concentrations of phosphatidyl inositol and calcium.

In preferred embodiments of the present invention, macrolide analogs according to the invention may be delivered to target tissues in the form of polymer or monoclonal antibody conjugate. Various polymer-based and antibody conjugate delivery systems are known and are currently being utilized in chemotherapeutic strategies. In the present invention, macrolide analogs may, for example, be chemically-modified to form poly(styrene-co-maleic acid)-conjugated macrolide analogs useful as therapeutics, particularly chemotherapeutics. In addition, analogs according to the present invention may be conjugated with monoclonal antibodies to form monoclononal antibody (MAb)-macrolide analog conjugates. The CD33 monoclonal antibody is illustrative of a useful Mab for this approach and may effectuate the targeting of a macrolide analog to cancerous tissues in various contexts, including in patients afflicted with acute myeloid leukemia. (See, e.g., Sievers et al., (1999) *Blood* 93: 3678.) As macrolide analogs according to the present invention exhibit extremely tight binding to actin, such analogs combined with a tissue or cell type targeting moiety are envisioned to be extremely specific in their mode of action thus avoiding the non-specific nature of currently available therapeutics (particularly, chemotherapeutics). Coupling of targeting agents to the 7'-hydroxyl position of the tris(oxazole)-containing macrolides (e.g., kabiramide C, see below) provides a particularly preferred approach as the 7'-hydroxyl of these compounds has been shown by the inventor to allow coupling of bulky chemical groups without effecting the biological activity of the macrolide analog (detailed in Examples section). Procedures for coupling such moieties to a molecule are well known in the art.

Analogs according to the invention include functional derivatives of kabiramide C wherein the 7'-hydroxyl position on the macrolide ring is modified with a methoxycoumarin (MC) or a diethylaminocoumarin (DEAC) group, as described in the following Example section. Particular analogs according to the invention, while being macrolide functional derivatives, are additionally useful in detecting and/or observing actin filaments. In preferred embodiments, these analogs are a tris(oxazole)-containing macrolide or functional derivatives thereof wherein the 7'-hydroxyl position on the macrolide ring is modified with a fluorescent moiety. In certain embodiments, the fluorescent moiety is a methoxycoumarin (MC) or a diethylaminocoumarin (DEAC) group.

Macrolide analogs useful in detecting actin filaments, as described and claimed herein, facilitate microscopy methods for observing actin filaments in which actin filaments are contacted with such analogs. Such microscopy methods are preferably carried out on actin filaments contained within living cells. Microscopy methods utilizing the macrolide analogs of the present invention are further envisioned to be offered in kit form. The Example section below demonstrates the preferred microscopy method utilizing preferred methoxycoumarin (MC) and diethylaminocoumarin (DEAC) labeled macrolides according to the present invention.

A more complete understanding of the invention can be obtained by reference to preferred embodiments of the invention which are illustrated by the following specific examples of compounds, compositions, and methods of the invention. These examples should not be construed as limiting. All percentages are by weight and all solvent mixture proportions are by volume unless otherwise noted. It will be apparent to those skilled in the art that the examples involve use of certain materials and reagents that are commercially available from known sources, e.g., chemical or biological material supply houses, so details regarding sources may thusly be absent.

EXAMPLES

INTRODUCTION: The molecular regulation of cell protrusion is a complex process involving as many as 100 different proteins and signaling molecules. In order to understand how the activities of these biomolecules are temporally and spatially regulated within the lamellipodium, it is necessary to use molecular tools and techniques to specifically perturb and monitor interactions related to G-actin and actin filaments. One approach, developed in the inventor's laboratory, uses light directed activation of caged ABPs to rapidly turn on the activity of specific ABPs at defined locations within a motile cell (Marriott et al, 1992; Roy et al, 2001; Marriott et al, 2003). A second approach employs pharmacological probes to specifically inhibit the activity or interactions of specific proteins within the actin cytoskeleton (Forscher and Smith, 1988).

In this disclosure, the present inventor establishes the actin-binding and inhibitory mechanisms for a family of cytotoxic, marine natural product macrolides. Evidence presented in this disclosure demonstrates that the inhibitory and cytotoxic effects of KabC and related macrolides are mediated through a combination actin binding modes involving novel mechanisms. In this disclosure, the inventor presents a detailed analysis of the different binding modes of KabC to G-actin and show how these interactions are responsible for KabC-mediated inhibition of actin filament dynamics and cytotoxicity. The functional studies reported in this disclosure demonstrate that free KabC (and related macrolides) acts as a novel biomimetic of Gelsolin, while the stable G-actin-KabC complex (and related macrolide complexes with G-actin) acts as a novel, unregulated (+)-end capping protein.

In particular, this study characterizes the interactions between Kabiramide C (KabC) and related macrolides and actin and establishes the mechanisms underlying their inhibition of actin filament dynamics and cytotoxicity. The fluorescence emission of G-actin, labeled at Cys374 with the environmentally sensitive fluorophore 6-proprionyl-2-dimethylaminonaphthalene (Prodan), is considerably perturbed on binding KabC and related macrolides. This fluorescence signal is used to show that the G-actin-KabC complex is extremely stable and long-lived and is formed through a two-step process involving a rapid binding of the macrolide ring of KabC to the actin surface, and a slower binding of the KabC tail with the cleft between sub-domains 1 and 3 of G-actin. Competition-binding studies show that KabC binds to the same site on G-actin as Gelsolin domain 1 (GS1) and CapG. KabC also binds to actin protomers within F-actin, which is followed by filament severing and capping of the new (+)-end. On the basis of these studies, the inventor demonstrates that free KabC and related macrolides act as small molecule biomimetics of Gelsolin. Furthermore, the stable G-actin-KabC complex is shown to incorporate onto the free (+)-end of an actin filament where it blocks further growth—this complex therefore functions as a novel, unregulated, actin filament (+)-end capping protein. Cells treated with low concentration of KabC (10 nM) and related macrolides for >12 hours fail to complete cytokinesis and are immotile. On the basis of these solution studies, the inventor demonstrates that these phenotypes result from the inhibition of (+)-end-directed actin filament growth by the G-actin-KabC complex. KabC and related macrolides represent the first examples of small molecule biomimetics of actin binding proteins. The discovery of novel actin binding and inhibitory mechanisms for KabC and related macrolides advances the understanding of the regulation of actin filament dynamics and provides a new therapeutic approach to treat diseases that arise from a dysfunctional regulation of the actin cytoskeleton as well as the basis of methods for identifying macrolide analogs.

Materials and Methods

Cell Culture: Rat bladder NBT-II carcinoma cells and mouse NIH 3T3 fibroblast cells are maintained and treated with external drugs as described in Choidas et al (1998).

Fluorescence spectroscopy: A customized SLM-Aminco AB2 fluorometer was used to record emission and excitation spectra of fluorescent dyes and their conjugates. Fluorescence emission spectra are recorded using excitation and emission polarizers aligned at 0° and 54° respectively and corrected for the instrument response (Marriott et al, 1988). Excitation anisotropy emission and excitation spectra are recorded according to Heidecker et al (1995). All spectra are recorded at room temperature.

Live cell microscopy: A multi-model microscope workstation was used to image phase contrast and fluorescence images of living cells (Choidas et al, 1998). Cells are maintained at 37° in a Hepes based culture medium in a Bioptechs cell perfusion chamber (Choidas et al, 1998).

Isolation and purification of macrolide drugs: The black sponge *Ircinia* sp. was collected off Sichang Island in the Gulf of Thailand on May 1997. The specimen (wet, 12 kg) was extracted three times with acetone (15 L) and the extract concentrated under vacuum to give an aqueous suspension. Following extraction with EtOAc and concentration the organic layer yields 69 g of dark oil. The oil was subjected to chromatographic separation using vacuum flash chromatography on silica gel, Sephadex LH20, and finally on ODS HPLC to give kabiramide C (450 mg), kabiramide B (180 mg) and several congeners. The kabiramides were identified based on the $^1$H and $^{13}$C NMR spectra, which are identical to those reported in the literature. A black unidentified sponge was collected off Iriomote Island, Okinawa on May 1998. The specimen (wet, 3 kg) was extracted three times with acetone (4 L) and the extract concentrated under reduced pressure to give an aqueous suspension. Following extraction with EtOAc and concentration the organic layer yields 15.2 g of oil. The oil is subjected to chromatographic separation using vacuum flash chromatography on silica gel, then on silica gel column, and finally on ODS HPLC to give halichondramide (382 mg). LatA, MisA, and SwiA are isolated from marine sponges as described by Jefford et al (1996), Kobayashi et al (1990), and Tanaka et al (1990). Scheuer (deceased) from the University of Hawai'i provided the sample of purified UlaA.

Cloning and gene expression: Genes encoding CapG and Gelsolin are cloned from a mouse brain cDNA library. Mouse Gelsolin and CapG genes are amplified by PCR using a mouse brain cDNA library (Invitrogen) as a template and gene specific primers and cloned in the HindIII, BamHI site of the pQE30 vector that has an N-terminal His-tag. DNA sequencing confirmed the sequence of genes. The M15 bacterial strain is used to express the genes.

Protein purification: A 1.6 L culture of bacteria expressing genes for CapG, Gelsolin or GS1 is induced with 1 mM IPTG at 30° or 37° for 5 to 6 h (FIG. 2A), then harvested and lysed using a combination of lysozyme and sonification on ice. All of the expressed proteins are soluble and the purification is carried out using Ni-NTA (Qiagen). About 50 mg of pure CapG is purified from a 600 ml culture.

F-actin: F-actin is purified from rabbit skeletal muscle using a standard protocol developed in the PI's laboratory (Marriott et al, 1988). The purity and activity of actin is analyzed using SDS-PAGE, polymerization assays and a motility assay (Heidecker et al, 1995).

Prodan-actin: Actin is labeled with the thiol probe, Acrylodan (Molecular Probes, Eugene, Oreg.) using a standard protocol (Marriott et al, 1988). Rabbit muscle G-actin is labeled with the thiol reactive, environmentally sensitive probe, Acrylodan, according to the inventor's earlier publication (Marriott et al, 1988). Briefly G-actin is dialyzed at 20 µM in G-buffer (2 mM Tris, 0.2 mM $CaCl_2$, 0.2 mM ATP, pH 8.0) without dithiothreitol (DTT) and treated with a 2-fold excess of Acrylodan (Molecular Probes) freshly prepared to 20 mM in DMF. The reaction is left in the dark for 1 hr at 20° and then dialyzed overnight at 4° against G-buffer containing 1 mM DTT. The labeled conjugate is polymerized for 90 minutes at 20° by adding $MgCl_2$ and KCl to 2 mM and 0.1 M respectively and centrifuged at 4° for 90 minutes at 100,000 g in a Beckman ultracentrifuge. The pelleted fluorescent actin conjugate is resuspended in G-buffer and dialyzed against 0.5 L G-buffer as described above. Prodan labeled G-actin is recovered from the supernatant fraction following a 100,000 g spin at 4°. Absorption spectroscopic analysis routinely shows that the labeling ratio of Prodan/actin monomer is 0.67. The emission maximum of Prodan-actin shifts during the polymerization of G-actin from 496 nm to 465 nm and is accompanied by an eight-fold increase in intensity at 465 nm (Marriott et al, 1988). Prodan-actin behaves as unlabeled actin in all functional assays tested (Marriott et al, 1988; Zechel, 1993; Roy et al, 2001).

Determination of the binding stoichiometry and dissociation constants for G-actin complexes with ABPs and macrolide drugs: The change in the quantum yield and/or emission energy of Prodan-actin is used to quantify the interaction of CapG and macrolides with G-actin. The stoichiometry of the CapG-G-actin and macrolide-G-actin complex is determined by titrating Prodan-G-actin at 1 µM with increasing amounts of CapG or the macrolide from $0.1{-}10$ µM. The volume of the macrolide or CapG added to the titration mixture is less than 2% of the total volume. The equilibrium binding constant is determined by titrating a constant amount of Prodan labeled G-actin at 0.05~0.1 µM in G- or F-buffer with incrementally increasing amounts of the macrolide or CapG over a range of 10 nM to 10 µM. The integrated intensity of Prodan-actin fluorescence under the spectrum is corrected for dilution effects. Control experiments show that the addition of up to 2% methanol to Prodan-G-actin has no effect on the emission spectrum or polymerization kinetics. The thermodynamic parameters for the equilibrium are determined from an analysis of these binding data using a standard binding algorithm (Johnson et al, 1988).

Kinetic analysis of binding reactions. The kinetics of the KabC interaction with Prodan-actin is determined, using an Applied Photophysics SX.18MV Stopped-flow spectrometer, by following the decrease in the emission intensity of Prodan-actin at 25° C. Prodan was excited at 385 nm and emission was collected with a 470 nm (+/−5 nm) band-pass filter. In all cases the decrease in emission intensity was best fit with a single exponential function, which was then used to determine the observed rate, $k_{obs}$. Kinetic constants of on rate ($k_{on}$) and off rate ($k_{off}$) were calculated according to the following equation: $k_{obs}=k_{on}[KabC]+k_{off}$. The kinetics of the slower binding step observed in the interaction of KabC with Prodan-G-actin interaction is measured by measuring the ratio of fluorescence signals at 465 nm and 530 nm. The decay of this ratio is fit using a single exponential rate.

Prodan-Actin Polymerization assay The fluorescence emission spectrum of a 5 µM solution of Prodan-labeled G-actin is recorded in G-buffer. Polymerization is initiated by adding KCl and $MgCl_2$ to 100 mM and 2 mM respectively and the time course of the reaction is monitored continuously over a 60-minute period time by recording the emission intensity at 465 nm. In other experiments the progress of actin polymerization is determined by recording the Prodan-actin emission spectrum at defined times during the reaction.

Prodan-actin Depolymerization Assay: The rate of Prodan-F-actin depolymerization is measured by recording the fluorescence signal 465 nm or by recording emission spectra at defined intervals during the 60-minute reaction.

Depolymerization is monitored following the dilution of a 5 µM solution of Prodan-labeled F-actin to 100 nM, i.e. below the 200 nM critical concentration, either in F-buffer. The kinetic parameters for the depolymerization of F-actin are determined from the decrease in fluorescence intensity at 465 nm (Marriott et al, 1988).

Characterization of actin binding proteins: The actin-binding properties of the ABPs used in this study are evaluated from changes in the fluorescence emission spectrum of Prodan-actin and actin polymerization assays as described by Marriott et al (1988).

Results and Discussion

High resolution Structures of G-Actin bound to KabC and Jaspisamide A. In summary, recent structural studies show that KabC and JspA mediate their interactions with actin through hydrophobic contacts involving two distinct structural moieties in the KabC molecule. The first such moiety is the macrolide ring, which exhibits considerable variations in its size and side groups and is firmly attached to surface of actin at the interface of sub-domains 1 and 3 through hydrophobic contacts with Ile341, Ile345, Ser348 and Leu349. Most of the polar side groups in the macrolide ring are directed towards the solvent while hydrophobic groups engage in specific apolar interactions with hydrophobic residues in actin. The second moiety is the long hydrophobic tail which is conserved in length having stereo-chemistry of its side groups that binds deeply within the cleft between sub-domains 1 and 3. The contacts made by the KabC tail within the actin cleft are primarily hydrophobic with major contributions from actin at residues Tyr143, Gly146, Thr148, Gly168, Tyr169, Ile345, Leu346, Thr351, Met355 and Phe375. The conserved water molecules seen in both the G-actin-KabC and G-actin JspA structures further stabilize the interaction of the tail with actin by bridging the terminal oxygen with the nitrogen of residues Tyr133, Ile136 and Ala170. The cleft region is also critical for the interaction of G-actin with GS1 (McLaughlin et al, 1993) and the axial actin protomer in the filament.

Prodan-actin: An environmentally sensitive actin conjugate. Amino acid residues close to Cys374 in actin are known to engage in specific interactions with structural elements of the (+)-end capping proteins, CapG, CP and GS1 (Doi et al, 1991) and the axial actin protomer in the actin filament. Fluorescence measurements of optical probes attached to the thiol group on Cys374 of actin can provide key information on molecular complexes of actin with ABPs or drugs. Pyrene-actin (Kouyama and Mihashi, 1981; Cooper et al, 1983) and Prodan-actin (Marriott et al, 1988) are the best characterized fluorescent actin conjugates. Marriott et al (1988) and Zechel (1993) have established the validity of Prodan-actin as a functional probe of actin and have shown that the fluorescence of this conjugate provides key information on changes in the molecular environment around Cys374 in response to ABP and/or drug binding. For example, the average energy of the fluorescence emission of Prodan in G-actin shifts from 496 nm (on a wavelength scale) to 465 nm for actin protomers within Prodan-F-actin and in the Prodan-actin-CapG complex (this study). On the other hand the binding of KabC to Prodan-G-actin decreases the quantum yield of the probe nearly 3-fold and red-shifts the emission maximum to 520 nm (FIG. 2A). Similar results are seen with other macrolides (data not shown). The sensitivity of the fluorescence emission of Prodan-actin to KabC binding reflects the close proximity of the probe to the macrolide ring-binding site. On the basis of earlier studies (Marriott, 1988; MacGregor and Weber, 1986; Weber and Farris, 1979), the inventor suggests that the binding of KabC to Prodan-G-actin involves a change in a specific dipolar interaction between the Keto-oxygen or the substituted amine on the probe and a peptide dipole within the actin matrix and/or, from a general solvent effect associated with an increased exposure of the probe to the high dielectric constant, aqueous solvent.

The macrolide-mediated red-shift in the fluorescence spectrum of Prodan-G-actin is used to determine key thermodynamic and kinetic parameters for this interaction. KabC, UlaA and Hal all bind to G-actin with a stoichiometry of 1:1 and exhibit a "dissociation constant" of 100 nM or less (FIG. 2A,B).

KabC and other trisoxazole macrolides bind to Prodan-G-actin in a two-step reaction. The kinetic parameters describing the interaction of Prodan-G-actin with KabC and related macrolide drugs are determined from analyses of the decrease in fluorescence emission of the actin conjugate at 480 nm. The primary binding event, which accounts for most of the fluorescence quenching and red-shift in Prodan-actin fluorescence, occurs at a rate of 30 s$^{-1}$ (FIG. 3A,B). Interestingly, the emission spectrum of the Prodan-actin-KabC complex shows a second, slower decrease in quantum yield and red-shift that evolve at a rate of 0.005 s$^{-1}$ (FIG. 3D). Related studies using Hal and UlaA show that the 1$^{st}$ and 2$^{nd}$-binding steps are common to all trisoxazole macrolides. Several lines of evidence, including dilution and competition-binding studies show that the final G-actin-KabC complex is extremely stable and does not dissociate at a concentration below the equilibrium constant, as might be expected for a simple binding reaction. This unusual property can be rationalized if it is assume that the second, slower binding event serves to kinetically trap the macrolide within the actin matrix. Since the primary binding event involves the rapid and relatively weak binding of the macrolide ring to the surface of actin, the inventor suggests that this second event reflects the tight binding of the long KabC tail within the actin cleft. The idea that the second binding reaction kinetically traps the drug is consistent with an analysis of the KabC-actin structure, which shows the tail emerges from the deep cleft to the actin surface after threading through Tyr169. Furthermore a structural analysis of all of stabilizing bonds in the KabC-G-actin complex would suggest that the tail contributes a significant amount to the total binding energy.

Figure 2:
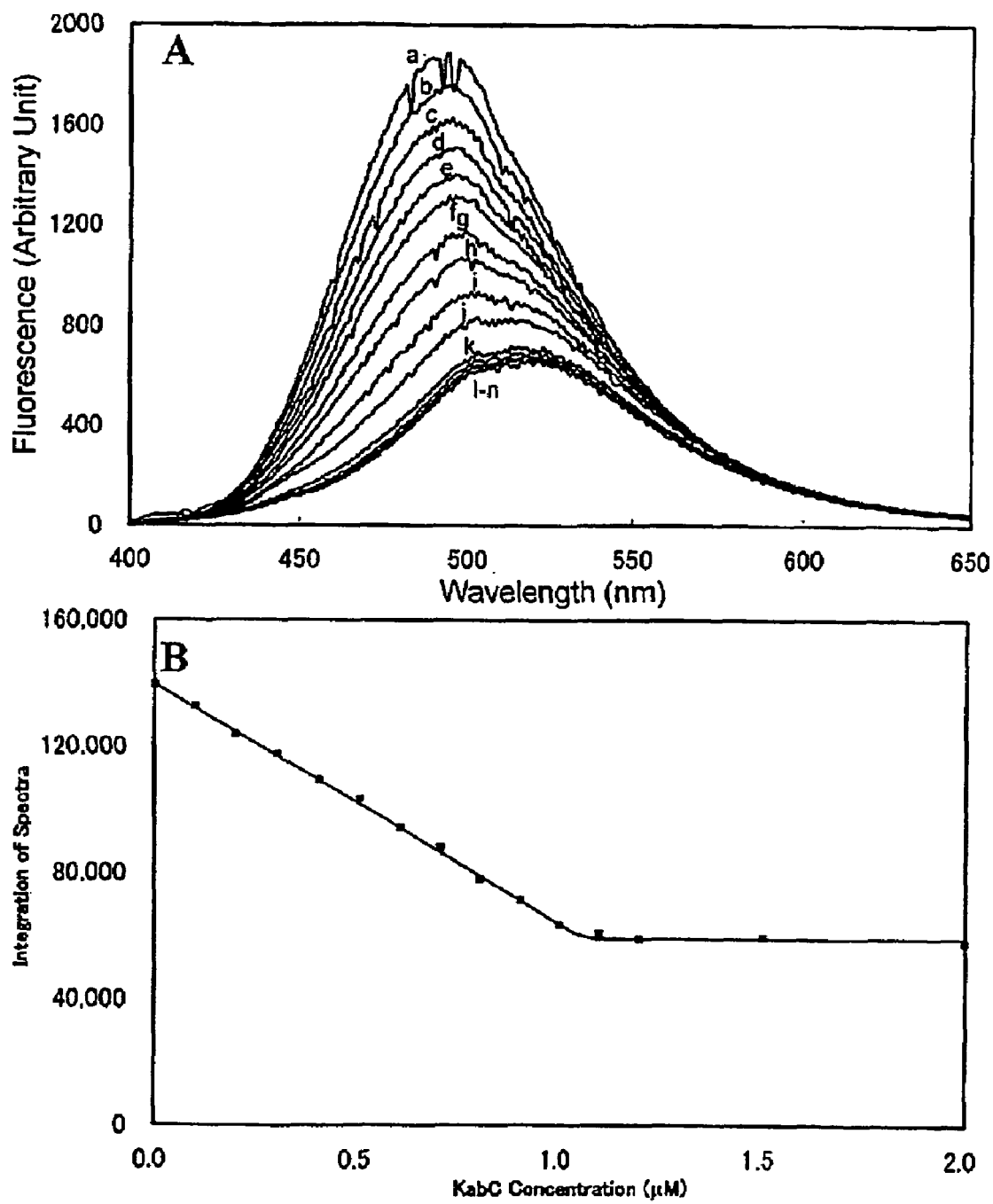
FIG. 2: (A), Stoichiometric binding of Prodan-labeled G-actin (1 μM) in G-buffer with KabC at final concentrations of in μm, a: 0.0; b: 0.1; c: 0.2; d: 0.3; e: 0.4; f: 0.5; g: 0.6; h: 0.7; i: 0.8; j: 0.9; k: 1.0; l: 1.1; m: 1.2; n: 1.5 (B), Plot of the integrated intensity in (A) against [KabC] yields a binding stoichiometry of 1:1.

Trisoxazolemacrolides specifically compete with GS1 for the (+)-end binding site on actin. Gelsolin, a monomeric 80 kD cytoskeleton protein composed of six domains interacts with actin filaments in a complex, Ca$^{2+}$-dependent manner (Janmey et al, 1985; Burtnick et al, 1997). Gelsolin exerts two major effects once bound to an actin filament: first it severs the filament and second it remains tightly bound to the severed (+)-end and serves to block, or cap, further growth. In vitro studies show that the interaction of Gelsolin with the (+)-end is very tight and long-lived, although the complex can be dissociated by PIP$_2$ (Janmey and Stossel, 1987; Chen et al, 1996). Structural analyses of G-actin complexes with GS1 (McLaughlin et al, 1993) and KabC show these unrelated molecules bind to G-actin through common contact sites that include a patch of hydrophobic residues on the surface between sub-domains 1 and 3 and within the cleft that forms between the interface of sub-domains 1 and 3 (McLaughlin et al, 1993;). GS1 binding to Prodan-G-actin shifts the average energy of the fluorescence emission to the red and is accompanied by a decrease in the quantum yield (FIG. 4A) but not to the extent seen in the KabC-G-actin complex (FIG. 2). The significant difference in the fluorescence emission spectra of Prodan-actin in its complexes with KabC and GS1 is exploited in a competition-binding assay to show that while KabC displaces GS1 from Prodan-G-actin in the presence of EGTA (FIG. 4A), GS1 cannot displace KabC from its complex with G-actin.

Figure 4:
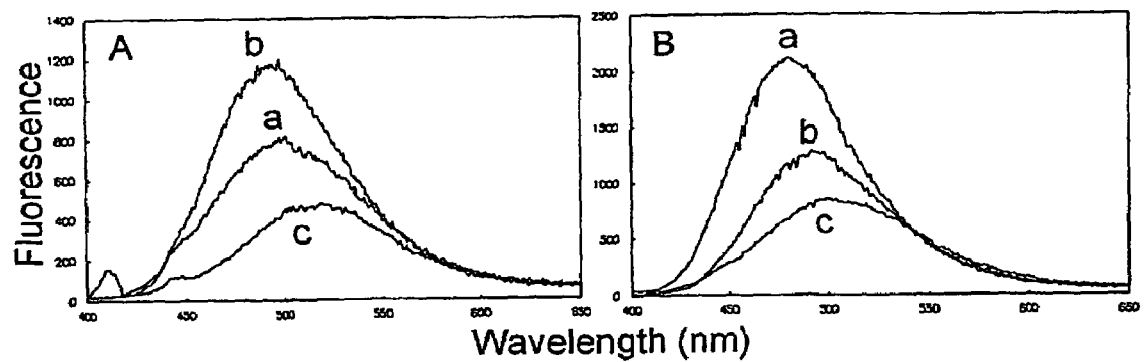
FIG. 4: (A) CapG: (a), Prodan-G-actin (100 nM), (b), Prodan-G-actin-CapG; (c), same as (b) in the presence of 0.2 μM KabC; (B); GS1: (a), Prodan-G-actin 100 nM; (b), Prodan-G-actin-GS1; (c), same as (b) in the presence of 0.2 μM KabC.

Trisoxazolemacrolides specifically compete with CapG for the (+)-end binding site on actin. CapG, a $Ca^{2+}$-dependent, (+)-end actin filament capping protein, is found at high levels in macrophage cells where it regulates membrane ruffling and cell protrusions associated with phagocytosis and motility (Botelho et. al., 2000). CapG contains only three of the six Gelsolin domains and is the only Gelsolin-like protein that does not sever actin filaments. The $Ca^{2+}$-dependent binding of CapG to Prodan-G-actin is accompanied by a dramatic blue-shift in the emission spectrum and an increase in quantum yield (FIG. 4B, curve b). The difference in fluorescence emission spectra between free and CapG-bound Prodan-G-actin is used to quantify the parameters for this binding reaction. The G-actin-CapG complex exists as a 1:1 complex and has a dissociation constant of 100 nM (data not shown). The dramatic difference in the fluorescence emission spectra of Prodan-actin in its complexes with CapG and KabC forms the basis of a competition-binding assay, which shows that KabC and related macrolides displace CapG from Prodan-G-actin in a $Ca^{2+}$-independent manner (FIG. 4B). A related assay is used to show that GS1 displaces CapG from its complex with Prodan-G-actin. Together these data show that CapG, GS1 and KabC and related macrolides share a common binding site on G-actin. This conclusion is consistent with a comparison of high-resolution structures of G-actin with GS1 and KabC and a preliminary analysis of a 2.8 Angstrom structure of a CapG mutant (Vorobiev et al, PDB database, 2002). Finally the competition-binding assay is used to demonstrate that the dimeric macrolides, SwiA and MisA, also bind to the same site on actin as KabC, CapG and GS1. However the emission properties of the CapG-Prodan-G-actin complex are unaffected by the binding of LatA, DNAse and thymosin β4 (Tβ4), which is consistent with some structural data showing that these sequestering molecules bind closer to the ATP pocket and DNAse binding loop (Kabsch et al, 1990).

Figure 5:
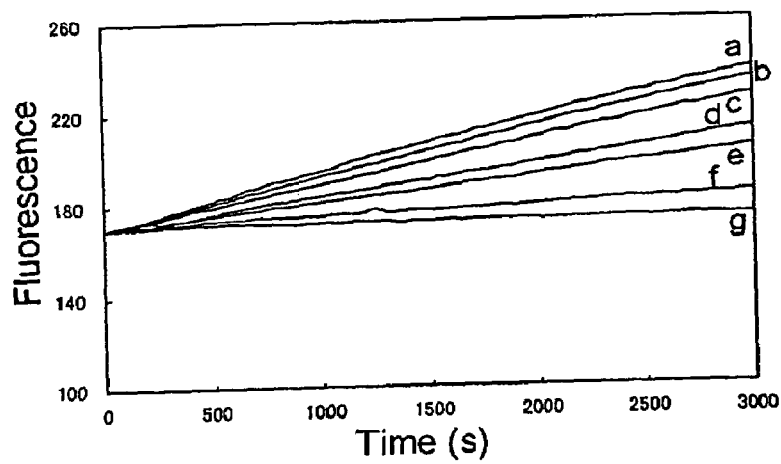
FIG. 5: Time course for G-actin polymerization. Prodan-labeled G-actin is mixed to a final concentration of 5 μM with a pre-formed complex of G-actin-KBC at the following concentrations: a: 0 nM; b: 1 nM; c: 5 nM; d: 10 nM; e: 20 nM; f: 50 nM; g: 250 nM) and the polymerization reaction initiated by the addition of KCl and $MgCl_2$ to 0.1 M and 2 mM respectively at 20°. Excitation at 385 nm and Emission at 465 nm.

The G-actin-KabC complex inhibits actin polymerization by capping the (+)-end of the filament. Most actin monomer sequestering proteins and drugs, such as Tβ4 (Roy et al, 2001) and LatA (Morton et al, 2000), engage in multiple, short-lived interactions with G-actin. These complexes usually exhibit a dissociation constant that is close to the critical concentration for actin polymerization (0.2 μM). The G-actin-KabC complex in comparison is extremely stable with a very long lifetime. The inventor showed that the cytotoxic effects of KabC seen at low concentration (>10 nM) are caused primarily by unique properties of the stable G-actin-KabC complex and do not involve multiple binding encounters of free KabC with G-actin. In this section the inventor tested the hypothesis that the KabC-G-actin complex prevents the incorporation of actin monomers onto the (+)-end of the filament by acting as an unregulated, (+)-end capping protein. To test this hypothesis the inventor performed an experiment to measure the rate of Prodan-G-actin polymerization in the presence of varying amounts of the pre-formed KabC-G-actin complex. In this assay a 5 μM solution of Prodan-G-actin in G-buffer is mixed with increasing amounts of pre-formed KabC-G-actin complex (from 1/5000~1/100 of the total G-actin). The amount of G-actin sequestered by KabC in this mixture is insignificant and does not change the critical concentration for actin polymerization of 0.2 μM. Adding KCl and $MgCl_2$ to 100 mM and 2 mM respectively polymerizes this G-actin mixture and the progress of the reaction is monitored by the increase in Prodan-actin fluorescence at 465 nm (FIG. 5; Marriott et al, 1988). The data show that trace levels of the G-actin-KabC complex dramatically reduce the rate and extent of actin polymerization (e.g FIG. 5, curve e). This result suggests that preformed G-actin-KabC decreases the rate of actin polymerization by binding to actin dimers and trimers during the nucleation phase and/or by capping of the (+)-end of filament during the elongation phase. Since the polymerization data do not show evidence that KabC-actin lengthens the early nucleation (lag) phase, the inventor demonstrates that the KabC-actin complex inhibits the rate of polymerization by binding to, and capping, the fast growing (+)-end of an elongating filament. On the basis of this study, the inventor proposes that complexes of G-actin with KabC and related macrolides inhibit actin filament dynamics by acting as novel, unregulated, (+)-end capping proteins.

Kabiramide and related macrolides bind to F-actin and lead to filament severing: Previous fluorescence studies using Pyrene labeled F-actin associate a macrolide-mediated decrease in pyrene fluorescence quantum yield to actin filament severing (Wada et al, 1998; Bubb et al, 1996; Terry et al, 1998). If true, then the instantaneous quenching seen in these studies would suggest that the macrolide-mediated severing of actin filaments is extremely efficient manner. However the key assumption that the decrease in quantum yield is a direct measure of filament severing actin is neither justified nor validated in these studies. The decrease the quantum yield of pyrene (or Prodan) could equally be caused by a macrolide-induced perturbation of the molecular environment of the probe that are unrelated to filament severing. The aforementioned assumption requires an independent determination of actin filament severing as described below.

Figure 6:
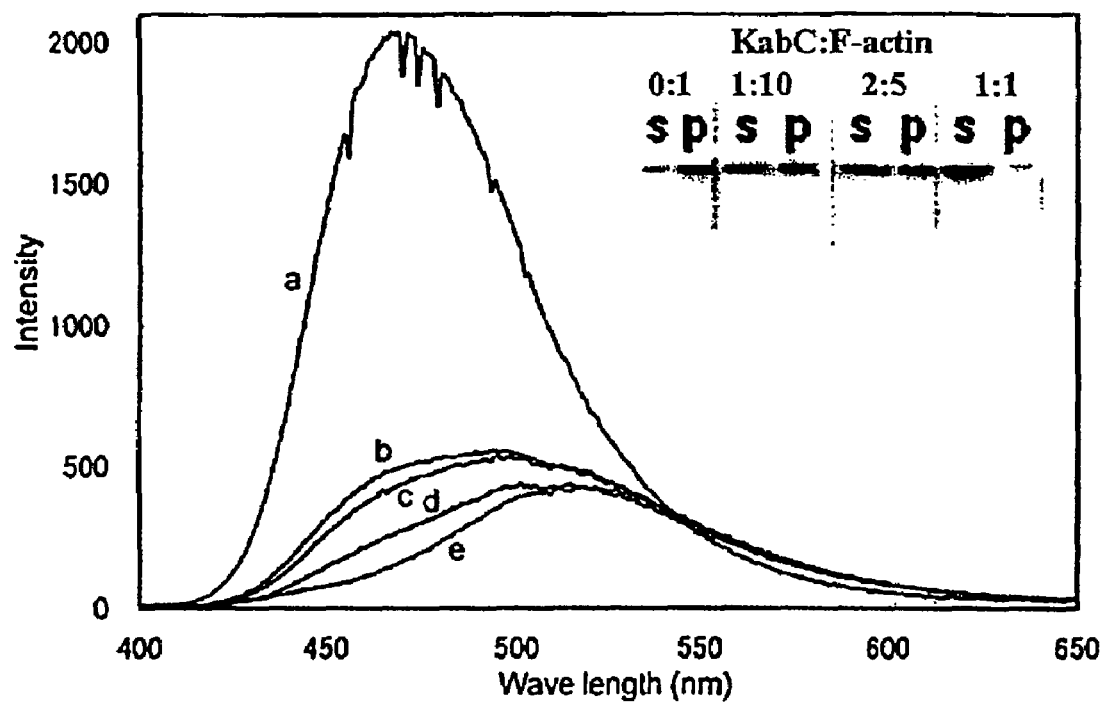
FIG. 6: Fluorescence emission spectra of 5 μM Prodan-F-actin in the absence (a), and after selected times following the addition of KabC to 5 μM: (b), immediately after the addition of KabC (the emission spectrum is acquired in 30 seconds); (c), 15 min; (d), 39 min; (e), The spectrum of an equivalent concentration of the KabC-Prodan-G-actin complex. Inset: SDS-PAGE Analysis of KabC binding to F-actin. 100 μL of F-actin (10 μM) in five tubes was treated each with KabC (a: 0; b: 1; c: 4; d: 10 μM) for 30 min and airfuged at 120,000 g for another 30 min. Supernatant (S) and pellet (P) of each sample was run on SDS-PAGE.
Figure 7:
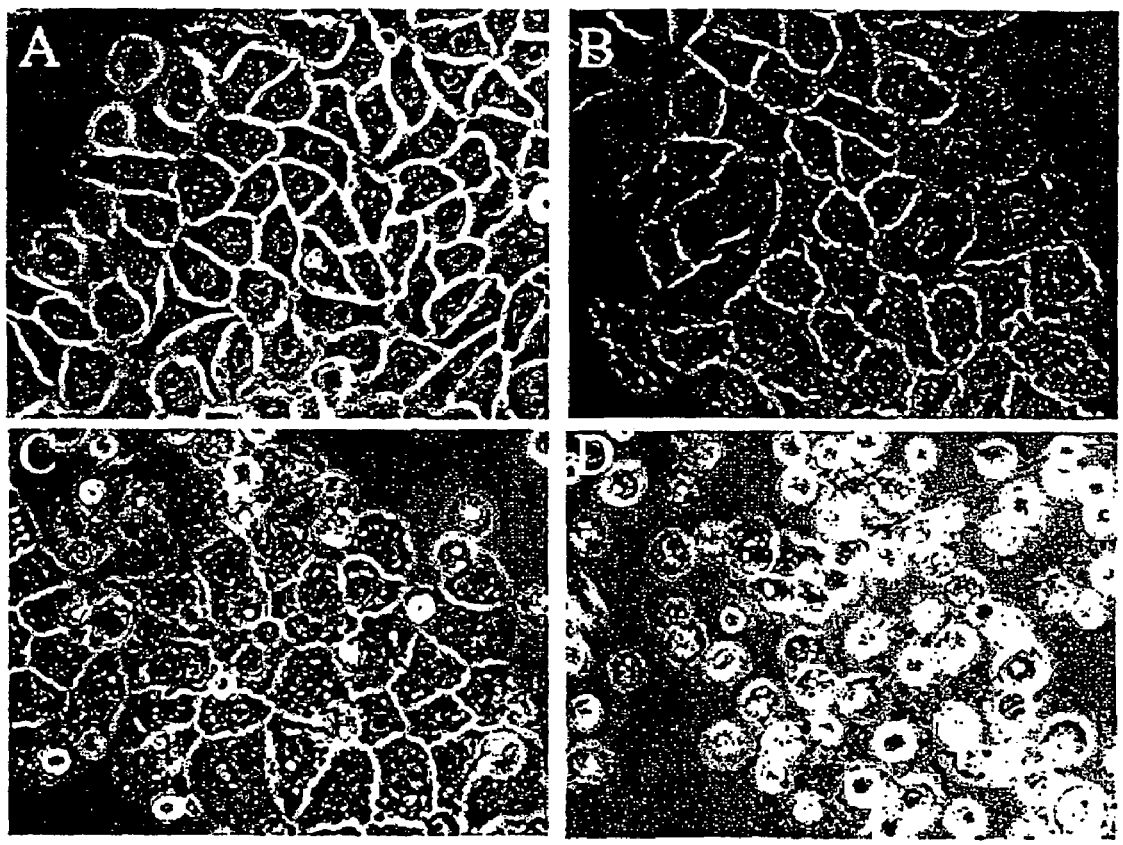
FIG. 7: Effect of KabC on NBT-II cells. NBT-II cells are imaged after 16 hours of drug treatment. KabC concentrations: (A), Control; (B), 10 nM; (C), 100 nM and (D), 1000 nM.

The fluorescence emission of Prodan-F-actin is also immediately quenched upon adding KabC (FIG. 7A). However, a particularly attractive feature of the Prodan-actin probe is that the average energy of the fluorescence emission changes appreciably following the binding of ABPs, macrolides and in the transition of F-actin to G-actin. Careful analysis of the spectrum can yield information on the relative amounts of up to 4 different states in equilibrium (Marriott et al, 1988). This feature is useful to help understand how KabC binds to Prodan-F-actin. The addition of an equimolar amount of KabC to Prodan-F-actin leads to an immediate decrease in the fluorescence quantum yield, which is followed by a far slower red-shift in the average energy of the emission spectrum over time. Even after 40 minutes the average energy of the emission does not reach the value expected for free Prodan-G-actin or the Prodan-G-KabC complex (FIG. 2A curve j). This result suggests that the immediate quenching of Prodan-F-actin fluorescence by equimolar KabC does not correlate with the rapid depolymerization of F-actin and the formation of the G-actin-KabC complex. Furthermore, the average energy of emission for Prodan-F-actin treated with a sub-stoichiometric amount of KabC (1/10th) is very similar to the control Prodan-F-actin spectrum (emission centered at 465 nm) and does not shift appreciably in time to the Prodan-G-actin spectrum (Data not shown). This result demonstrates that F-actin is not depolymerized by sub-stoichiometric levels of KabC as might be expected for a drug that engages in multiple binding and severing events with the filament. This result can also be seen in an SDS-PAGE analysis of the same Prodan-F-actin/KabC mixtures. In this experiment, the monomeric actin (supernatant, S) and F-actin (pellet, P) fractions of KabC treated F-actin are separated after a 60-minute incubation by high-speed centrifugation (120,000 g) and quantified by Coumassie staining of the acrylamide gel. The data shown in FIG. 6 show that the amount of monomeric G-actin and filamentous F-actin in these samples correlates with the amount of KabC (FIG. 6B). For example in the samples containing F-Actin:KabC at a ratio of 10:1 and 5:2, the inventor finds that a significant fraction of the total actin exists as F-actin (FIG. 6B, curves b,c). If KabC were to engage in multiple and rapid binding and severing events with the filament, then the majority of the actin in these samples would appear in the supernatant fraction. Furthermore, the inventor deduces from these particular data that the KabC-mediated severing reaction is slow, otherwise most of the actin would be present in the supernatant fraction (e.g. in 6Bc, the average filament would contain 2.5 actin protomers). Together these studies show that while KabC binds rapidly to Prodan-F-actin it only engages in a single and slow severing event and results in the KabC binding strongly to the actin protomer at the (+)-end of the severed filament where it blocks further filament growth.

From analyses of the interaction of KabC with F- and G-actin using fluorescence assays, kinetic, SDS-PAGE and structural studies reported herein, the inventor proposes a 2-step reaction mechanism to explain the severing of actin filaments by KabC and related macrolides (Summarized in FIG. 8C). First, the macrolide ring of KabC binds rapidly to the exposed hydrophobic patch on an actin protomer in the filament. Consistent with this hypothesis, structural models of F-actin show that the macrolide ring binding site on actin protomers is exposed on the filament. The rapid binding of KabC to Prodan-F-actin results in an immediate decrease in the quantum yield (presumably the same holds true for pyrene-F-actin)—however, this primary binding event does not sever the actin filament. Second, the binding of the macrolide ring to the actin protomer positions the KabC tail so that it can compete for the binding site within the cleft between domains 1 and 3 with the axial actin protomer. This reaction is slow but eventually the KabC tail displaces the hydrophobic plug of the axial actin protomer, which weakens the bond between adjacent protomers and leads to filament severing. KabC remains strongly bound to the actin protomer at the (+)-end of the severed filament. The interaction between KabC and the actin protomer of the severed filament is very long and so the macrolide is only involved in a single severing event. The KabC bound actin protomer prevents the incorporation of new actin monomers and consequently functions as a (+)-end capping protein complex. The severing and capping activities of KabC are very similar to those observed for Gelsolin and on this basis the inventor proposes that the free form of KabC and related macrolides act as small molecule biomimetics of Gelsolin.

Trisoxazole macrolides exhibit concentration dependent effects on the cell cytoskeleton. KabC, UlaA, Hal and the dimeric macrolides, MisA and SwiA, exhibit a concentration dependent cytotoxic activity on NBT II epithelia cells. These results are summarized for KabC in FIG. 8 (A-D). Cells treated with KabC or related macrolides at a concentration of 1 µM or higher experience a complete breakdown of their actin cytoskeleton and die within a few hours (FIG. 8D). On the other hand cells treated with 10~100 nM KabC show cytoskeleton-linked phenotypes that include a loss of actin-associated cell-cell contacts in adherens junctions, defective cytokinesis as revealed by polyploidy, an increase in the size and number of intracellular vacuoles, a loss of cell motility, existence of cell blebbing and massive accumulation of F-actin at the cell cortex (FIG. 7C,D; data not shown). These phenotypes suggest that cells treated with a low concentration of macrolide exhibit a dysfunctional regulation of actin filament dynamics. These phenotypes are not observed in untreated, control cells.

While not being bound to one particular theory, the inventor interprets these concentration-dependent effects as follows: The macrolide enters the cell and at high concentration the free form of the drug mediates the complete disassembly of the actin cytoskeleton through a combination of actin filament severing and G-actin monomer sequestering while the G-actin-KabC complex blocks the growth of new actin filaments. At lower concentration the macrolide binds primarily to G-actin monomer within the cell and this complex, once incorporated onto a elongating filament blocks any further growth from the (+)-end during cell protrusion (Theriot and Mitchison, 1991), during the formation of the cleavage furrow (Glover et al, 2002) and during the transport of endosomes and other intracellular vesicles (Defacque et al, 2000; Rozelle et al, 2000). The inventor proposes that the premature capping of actin filaments by the G-actin-KabC complex leads to shorter actin filaments that fail to function correctly during cell motility, cytokinesis and vesicle transport.

Macrolide Functional Derivatives. A review of the literature and a screen of chemical databases shows that while all of the putative actin-binding drugs contain a macrolide ring, the nature and position of the side groups and the size of the ring varies considerably (FIG. 1A-E). For example, the inventor shows in FIG. 1 that the scytophycins (Ishibashi et al, 1986), typified by tolytoxin (Carmeli et al, 1990), have a smaller macrolide ring and lack the trisoxazole moiety. Other classes of macrolide that lack a trisoxazole group, shown in FIG. 1, include aplyronines (Yamada et al, 1993), sphinxolides (Guella et al, 1989), and reidispongiolides (D'Auria et al, 1994). The inventor has shown that the initial binding of the macrolide ring to actin positions the tail so that it can bind within the deep, hydrophobic cleft between sub-domains 1 and 3 in actin. Interestingly, all of the macrolide drugs identified from the inventor's search of related structures contain a hydrophobic tail of identical length with similarly disposed apolar side groups. The structural studies suggest that this preferred stereochemistry is dictated by the allowable interactions of the apolar groups in the tail within the actin cleft. The slow binding of the tail within the cleft is associated with equally conformational transitions in actin that must occur to accommodate these apolar groups. Furthermore, these slower binding events serve to kinetically trap the macrolide and account for the remarkable stability and lifetime of actin-macrolide complex.

Figure 1:
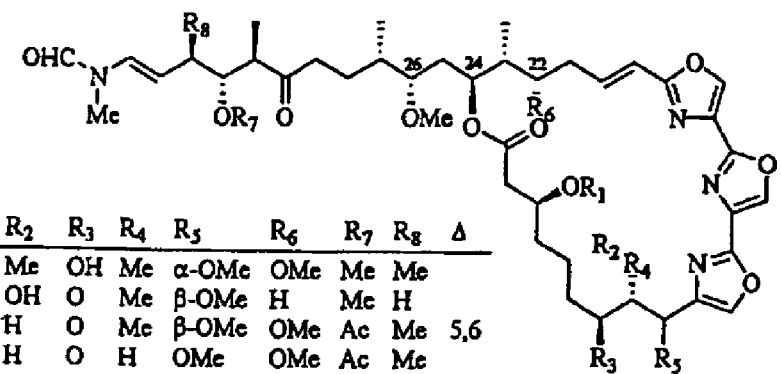
FIG. 1: Molecular structure of Kabiramide and related trisoxazole macrolides as well as structures of related macrolides that inhibit actin filament dynamics through a similar mechanism as described for the trisoxazole macrolides.
Figure 1:
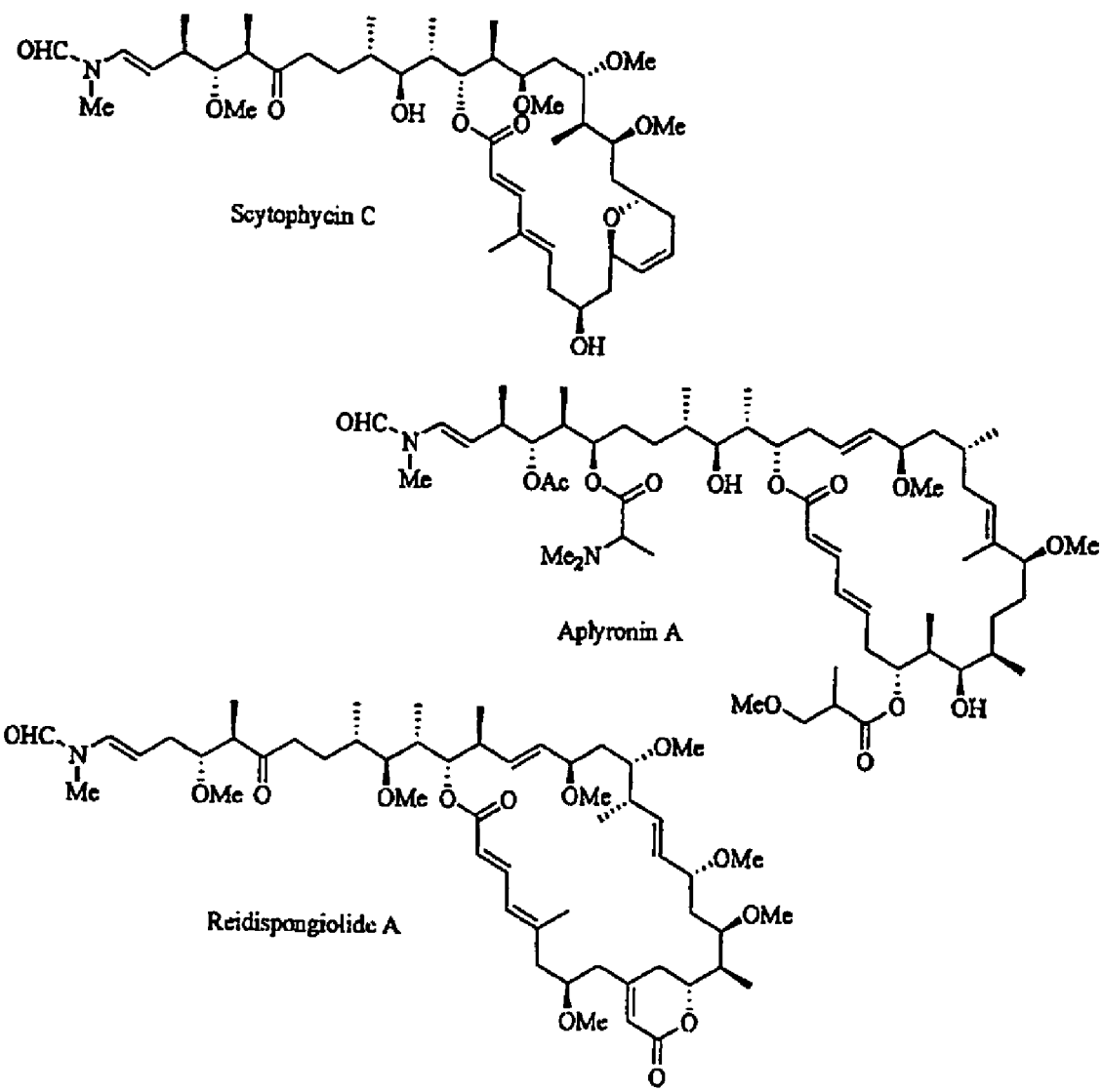
Figure 3:
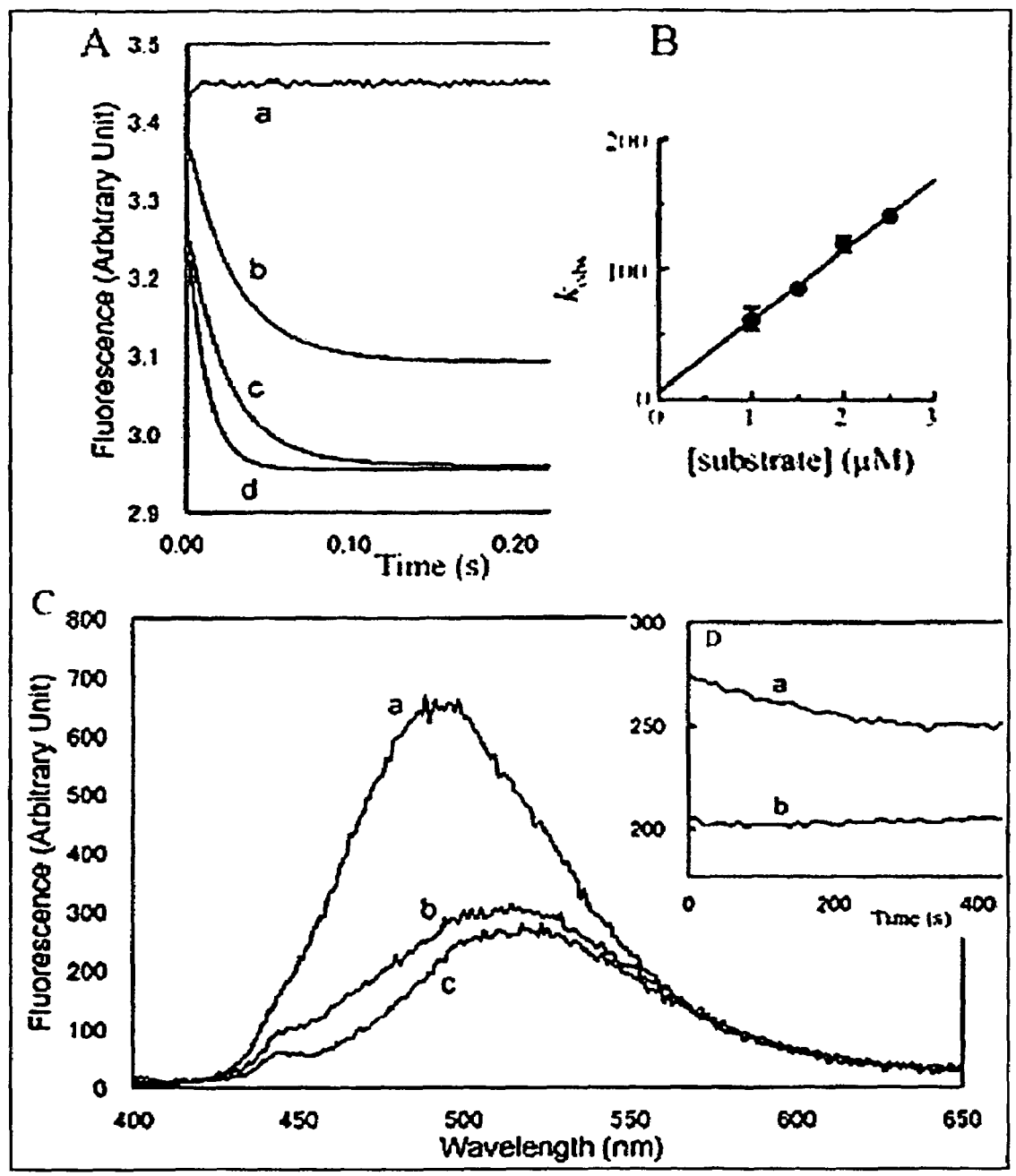
FIG. 3: Kinetic analyses of KabC binding of Prodan labeled G-actin. (A-B). Prodan-actin (0.1 μM) and KabC, loaded into separated syringes, were rapidly mixed within ~1 msec dead-time. The concentrations of KabC were 0.0 μM (a), 1.0 μM (b), 1.5 μM (c), 2.0 μM (d) and 2.5 μM (data not shown), respectively. The decreases in emission intensity were well fitted with single exponential functions to determine the observed rate, $k_{obs}$. The observed rates are plotted as a function of the [KabC] in panel (B). The Y-intercept and the slope yield $k_{off}$ (5.6 (5.9 $sec^{-1}$) and $k_{on}$ (54.5 (3.2×10$^6$ $M^{-1}sec^{-1}$), respectively. These kinetic constants give rise to a "dissociation constant" ($K_d$) of ~0.1 μM. (C), The emission spectrum of 0.1 μM Prodan-G-actin (a), is red-shifted and lower in intensity (b), soon after mixing KabC. The same sample exhibits a further red-shift seen after 5 minutes as seen in spectrum (c). (D), The second, slower phase of the G-actin-KabC binding reaction is revealed by monitoring the specific decrease in the blue edge of the spectrum 465 nm (curve a) with respect to the red edge (550 nm, curve b) from which the inventor calculates a rate of 0.008 $s^{-1}$.

A fluorescent Dansyl derivative of KabC linked to the end of the tail does not bind to G-actin (data not shown; see also Wada et al, 1998). This property is consistent with the analysis of the crystal structure of KabC-actin, which show that bulky groups in the KabC tail would hinder the interaction with the actin cleft. However, the crystal structure of KabC-actin reveals that the 7'-hydroxyl group on the macrolide ring is exposed to the solvent and does not contribute to the interaction with G-actin (FIG. 1). To test this hypothesis, the inventor modified this hydroxyl group with acylazide derivatives of methoxycoumarin (MC) and diethylaminocoumarin (DEAC). These fluorescent derivatives were prepared on a small scale (see methods section). The binding of either MC-KabC or DEAC-KabC to unlabeled G-actin increases the fluorescence quantum yield of the coumarin probe (2.57 and 4.0 fold respectively) and is accompanied by a red shift in the emission spectrum (FIG. 2A,B). A time-resolved fluorescence analysis of the interaction of DEAC-KabC with G-actin shows the presence of two-binding steps (FIG. 3A) and supports the conclusions drawn from the Prodan-G-actin kinetic studies (data not shown). DEAC-KabC was also shown to bind to unlabeled G-actin by recording the change in the fluorescence polarization (FP) value—the FP value for free DEAC-KabC increases from 0.063+/−0.02 in G-buffer to 0.183+/−0.02 when bound to G-actin. Consistent with the inventor's conclusions on the remarkable stability of the KabC-actin complex, the pre-formed DEAC-KabC actin complex does not dissociate in the presence of a large excess CapG (FIG. 2B). Preliminary confocal imaging data on a KabC derivative linked to fluorescein diacetate within living NBT-II cells shows that the fluorescent probe associates with sites of actin filament dynamics and cell protrusion (FIG. 3).

Preparation of Kabiramide C-diethylaminocoumarin derivative. A mixture of KabC (0.28 mg, 0.3 (mol), 7-diethylaminocoumarin-3-carbonylazide (0.43 mg, 1.5 (mol) in $CH_2Cl_2$ (180 (L) was taken in a sealed glass tube, and the mixture was heated at 65 C for 18 h. The reaction product gave two spots (KabC and its fluorescent derivative in nearly 1-1 ratio) on tlc. After separation on preparative tlc (silica, $CH_2Cl_2$-MeOH, 20−1), a fluorescent derivative (ca. 0.1 mg) was obtained. ESIMS m/z 1222 [M+Na]+.

Preparation of Kabiramide C-F6218 (fluorescein diacetate) derivative. A mixture of KabC (0.28 mg, 300 nmol), fluoscein-5-carbonyl azide, diacetate (F6218, 0.73 mg, 1.5 (mol, Molecular Probe) in $CH_2Cl_2$ (180 (L) was taken in a sealed glass tube, and the mixture was heated at 65 C for 18 h. The reaction product showed nearly one spot on tlc. After separation on preparative tlc (silica, $CH_2Cl_2$-MeOH, $20^{-1}$), a fluorescent derivative (ca. 0.2 mg) was obtained. ESIMS m/z 1421 [M+Na]+.

Summary

The binding studies reported in this study along with an recent investigation on high resolution structures of G-actin complexes with trisoxazole macrolides identify two structural determinants in KabC and other trisoxazole macrolide drugs that underlie their potent cytotoxicity: (1), the hydrophobic macrolide ring and (2), the long, hydrophobic tail with stereochemically defined side groups. The unique environmentally sensitive actin conjugate, Prodan-actin, allows spectroscopic studies distinguish the binding of these two determinants to G-actin and to assign likely functions for each binding event. First, the rapid binding of the macrolide ring to the surface of actin at the entrance to the cleft between sub-domains 1 and 3 is mediated by specific hydrophobic interactions. Interestingly the (+)-end binding ABPs CapG and GS1 share common contact residues at this surface site. Given the fact that these ABPs bind to the actin protomer at the (+)-end of the actin filament through the same contact residues, it is useful to describe this region of the actin monomer as the (+)-end. The rapid binding of the macrolide to the (+)-end of the actin monomer is accompanied by the rapid quenching and red-shift of Prodan-actin fluorescence spectrum and suggests that the dipolar environment around the Prodan molecule changes significantly during this initial binding event.

The different binding modes of KabC and related trisoxazole macrolides to monomeric actin and actin protomers in a filament are schematized in FIG. 8 (A-C). Actin filament dynamics is inhibited by KabC through the effects of different modes of actin binding:

(A), Monomer Sequestering. In vitro studies using stoichiometric binding conditions show that the KabC and related macrolides sequester actin monomers and raise the critical concentration for actin polymerization, (FIG. 2B); (B), (+)-end filament capping In vitro studies show that the very stable KabC-G-actin complex can incorporate onto the (+)-end of an elongating actin filament but the KabC in the (+)-end bound protomer blocks the further addition of actin monomers onto the filament; (C), Filament Severing; KabC and related macrolides bind to actin protomers in the filament and sever the filament at that site in a two-step reaction. The KabC drug remains bound to the actin protomer at the (+)-end of the severed filament where it caps further filament growth. Severing by KabC is mediated by the binding of the macrolide ring to its surface site on a protomer in the filament, which allows the tail to compete with the axial actin protomer for the cleft binding site. Once the tail is bound to the cleft the actin-actin bond is disrupted and the filament severs at that site with the drug remaining firmly bound to the (+)-end protomer which acts as an unregulated capping complex.

In summary, this work has established that members of the macrolide family, particularly trisoxazole-containing macrolides, and related drugs inhibit actin filament dynamics through novel mechanisms. Knowledge of the structural principles governing the interactions of macrolides with actin together with a understanding of their cytotoxicity will prove useful in designing and identifying related classes of natural and synthetic drugs to study the regulation of actin filament dynamics in motile cells and will lead to the development of a new class of biomimetic therapeutics to treat cancer and other diseases caused by dysfunctional regulation of the actin cytoskeleton.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

REFERENCES

Asch, H. L., K. Head, Y. Dong, F. Natoli, J. S. Winston, J. L. Connolly, and B. B. Asch. 1996. Widespread loss of gelsolin in breast cancers of humans, mice, and rats. *Cancer Res.* 56:4841-4845.

Bamburg, J. R., and O. P. Wiggan. 2002. ADF/cofilin and actin dynamics in disease. *Trends Cell Biol.* 12:598-605.

Barkalow, K., W. Witke, D. J. Kwiatkowski, and J. H. Hartwig. 1996. Coordinated regulation of platelet actin filament barbed ends by gelsolin and capping protein. *J. Cell Biol.* 134:389-399.

Botelho, R. J., M. Teruel, R. Dierckman, R. Anderson, A. Wells, J. D. York, T. Meyer, and S. Grinstein. 2000. Localized biphasic changes in phosphatidylinositol-4,5-bisphosphate at sites of phagocytosis. *J. Cell Biol.* 151:1353-1368.

Bubb, M. R., I. Spector, A. D. Bershadsky, and E. D. Korn. 1995. Swinholide A is a microfilament disrupting toxin that stabilizes actin dimers and severs actin filaments. *J. Biol. Chem.* 270:3463-3466.

Burtnick, L. D., E. K. Koepf, J. Grimes, E. Y. Jones, D. I. Stuart, P. J. McLaughlin, and R. C. Robinson. 1997. The crystal structure of plasma gelsolin: Implications for actin severing, capping, and nucleation. *Cell.* 90:661-670.

Carmeli, S., R. E. Moore, and G. M. L. Patterson. 1990. Tolytoxin and new scytophycins from three species of *Scytonema*. *J. Nat. Prod.* 53:1533-1542.

Chen, P., J. E. Murphy-Ullrich, and A. Wells. 1996. A role for gelsolin in actuating epidermal growth factor receptor-mediated cell motility. *J. Cell Biol.* 134:689-698.

Choidas, A., A. Jungbluth, A. Sechi, J. Murphy, A. Ullrich, and G. Marriott. 1998. The suitability and application of a GFP-actin fusion protein for long-term imaging of the organization and dynamics of the cytoskeleton in mammalian cells. *Eur. J. Cell Biol.* 77:81-90.

Cooper J. A., S. B. Walker, and T. D. Pollard. 1983. Pyrene actin: documentation of the validity of a sensitive assay for actin polymerization. *J. Muscle Res. Cell Motil.* 4:253-262.

Cooper, J. A. and D. A. Schafer. 2000. Control of actin assembly and disassembly at filament ends. *Curr. Op. Cell Biol.* 12:97-103.

D'Auria, M. V., L. G. Paloma, L. Minale, A. Zampella, J.-F. Verbist, C. Roussakis, C. Debitus, and J. Patissou. 1994. Reidispongiolide A and B, two new potent cytotoxic macrolides from the New Caledonian sponge *Reidispongia coerulea*. *Tetrahedron*. 50:4829-4834.

Defacque H, M. Egeberg, A. Habermann, M. Diakonova, C. Roy, P. Mangeat, W. Voelter, G. Marriott, J. Pfannstiel, H. Faulstich, and G. Griffiths. 2000. Involvement of ezrin/moesin in de novo actin assembly on phagosomal membranes. *EMBO J.* 19:199-212.

Doi, Y., M. Banba, and A. Vertut-Doi. 1991. Cysteine-374 of actin resides at the gelsolin contact site in the EGTA-resistant actin-gelsolin complex, *Biochemistry.* 30:5769-5777.

Forscher, P., and S. J. Smith. 1988. Actions of cytochalasins on the organization of actin filaments and microtubules in a neuronal growth cone. *J. Cell Biol.* 107:1505-1516.

Guella, G., I. Mancini, G. Chiasera, and F. Pietra. 1989. Sphinxolide, a 26-membered antitumoral macrolide isolated from an unidentified Pacific nudibranch. *Helv. Chim. Acta.* 72:237-246.

Heidecker, M., Y. Yan-Marriott, and G. Marriott. 1995. Proximity relationships and structural dynamics of the phalloidin binding-site of actin-filaments in solution and on single actin-filaments on heavy meromyosin. *Biochemistry.* 34:11017-11025.

Ishibashi, M., R. E. Moore, G. M. L. Patterson, C. Xu, and J. Clardy. 1986. Scytophycins, cytotoxic and antimycotic agents from the cyanophyte *Scytonema pseudohofmanni*. *J. Org. Chem.* 51:5300-5306.

Janmey, P. A., C. Chaponnier, S. E. Lind, K. S. Zaner, T. P. Stossel, and H. L. Yin. 1985. Interactions of gelsolin and gelsolin-actin complexes with actin. Effects of calcium on actin nucleation, filament severing, and end blocking. *Biochemistry.* 24:3714-3723.

Janmey, P. A., K. Iida, H. L. Yin, and T. P. Stossel. 1987. Polyphosphoinositide micelles and polyphosphoinositide-containing vesicles dissociate endogenous gelsolin-actin complexes and promote actin assembly from the fast-growing end of actin filaments blocked by gelsolin. *J. Biol. Chem.* 262:12228-12236.

Jefford, C. W., G. Bernardinelli, J. Tanaka, and T. Higa. 1996. Structures and absolute configurations of the marine toxins, latrunculin A and laulimalide, *Tetrahedron Lett.* 37:159-162.

Johnson, N., G. Marriott, and K. Weber. 1988. p36, the major cytoplasmic substrate of src tyrosine protein kinase, binds to the p11 regulatory subunit via a short amino-terminal amphiphatic helix. *EMBO. J.* 7:2435-2442.

Kabsch, W., H. G. Mannherz, D. Suck, E. F. Pai, and K. C. Holmes. 1990. Atomic structure of the actin-DNase I complex. *Nature*. 347:37-44.

Kobayashi, M., J. Tanaka, T. Katori, M. Miki, M. Yamashita, and I. Kitagawa. 1990. Marine natural products. XXII. The absolute stereostructure of swinholide A, a potent cytotoxic dimeric macrolide from the Okinawan marine sponge *Theonella swinhoei*. *Chem. Pharm. Bull.* 38:2409-2418.

Kouyama, T., and K. Mihashi. 1981. Fluorimetry study of N-(1-pyrenyl) iodacetamide-labelled F-actin. Local structural change of actin protomer both on polymerization and on binding of heavy meromyosin. *Eur. J. Biochem.* 114:33-38.

Macgregor, R. B. and G. Weber. 1986. Estimation of the polarity of the protein interior by optical spectroscopy. *Nature*. 319:70-73.

Marriott, G., 1987. PhD Thesis. Protein dynamics: a fluorescence spectroscopic approach. University of Illinois-Urbana-Champaign.

Marriott, G., K. Zechel, and T. M. Jovin. 1988. Spectroscopic and functional characterization of an environmentally sensitive fluorescent actin conjugate. *Biochemistry.* 27:6214-6220.

Marriott, G., H. Miyata, and K. Kinosita. 1992. Photomodulation of the nucleating activity of a photocleavable cross-linked actin dimer. *Biochemistry Int.* 26:943-951.

Marriott, G., P. Roy, and K. Jacobson. 2003. Preparation and light-directed activation of caged proteins. In Biophotonics. Meth Enzymol. Editors G. Marriott and I. Parker. 360, 274-288.

Matsunaga, S.; N. Fusetani, K. Hashimoto, K. Koseki, and M. Noma. 1986. Kabiramide C, a novel antifungal macrolide from nudibranch eggmasses. *J. Am. Chem. Soc.* 108:847-849.

McLaughlin, P. J., J. T. Gooch, H. G. Mannherz, and A. G. Weeds. 1993. Structure of gelsolin segment-1-actin complex and the mechanism of filament severing. *Nature*. 364:685-692.

Morton, W. M., K. R. Ayscough, and P. J. McLaughlin. 2000. Latrunculin alters the actin-monomer subunit interface to prevent polymerization. *Nature Cell Biol.* 2:376-378.

Pollard, T. D. 2003. The cytoskeleton, cellular motility and the reductionist agenda. *Nature*. 422:741-745.

Roesener, J. A., and P. J. Scheuer. 1986. Ulapualide A and B, extraordinary antitumor macrolides from nudibranch eggmasses. *J. Am. Chem. Soc.* 108:846-847.

Roy, P., Z. Rajfur, D. Jones, G. Marriott, L. Loew, and K. Jacobson. 2001. Local photorelease of caged thymosin β4 in locomoting keratocytes causes cell turning. *J. Cell Biol.* 153:1035-1048.

Rozelle, A. L., L. M. Machesky, M. Yamamoto, M. H. E. Driessens, R. H. Insall, M. G. Roth, K. Luby-Phelps, G. Marriott, A. Hall, and H. L. Yin. 2000. Phosphatidylinositol 4,5-bisphosphate induces actin-based movement of raft-enriched vesicles through WASP-Arp2/3. *Curr. Biol.* 10:311-320.

Saito, S., and H. Karaki. 1996. A family of novel actin-inhibiting marine toxins. *Clin. Exp. Pharm. Physiol.* 23:743-746

Tanaka, J., T. Higa, M. Kobayashi, and 1. Kitagawa. 1990. Marine natural products. XXIV. The absolute stereostructure of misakinolide A, a potent cytotoxic macrolide from an Okinawan marine sponge *Theonella* sp. *Chem. Pharm. Bull.* 38:2967-2970.

Terry, D. R., I. Spector, T. Higa, and M. R. Bubb. 1997. Misakinolide A is a marine macrolide that caps but does not sever filamentous actin. *J. Biol. Chem.* 272:7841-7845.

Theriot, J. A., and T. J. Mitchison. 1991. Actin microfilament dynamics in locomoting cells. *Nature.* 352:126-131.

Witke, W., Sharpe, A. H., Hartwig, J. H., Azuma, T., Stossel, T. P. and Kwiatkowski, D. J. (1995). *Cell.* 81(1) 41-51

Wada, S.; S. Matsunaga, S. Saito, N. Fusetani, and S. Watabe. 1998. Actin-binding specificity of marine macrolide toxins, mycalolide B and kabiramide D. *J. Biochem.* 123:946-952.

Weber, G., and F. J. Farris. 1979. Synthesis and spectral properties of a hydrophobic fluorescent probe: 6-propionyl-2-(dimethylamino) naphthalene. *Biochemistry* 18:3075-3078

Witke, W., J. D. Sutherland, A. Sharpe, M. Arai, and D. J. Kwiatkowski. 2001. Profilin I is essential for cell survival and cell division in early mouse development. *Proc. Natl. Acad. Sci. USA.* 98:3832-3836.

Yamada, K., M. Ojika, T. Ishigaki, Y. Yoshida, H. Ekimoto, and M. Arakawa. 1993. Aplyronine A, a potent antitumor substance, and the congeners aplyronines B and C isolated from the sea hare *Aplysia kurodai. J. Am. Chem. Soc.* 115:11020-11021.

Zechel, K. 1993. The interaction of 6-propionyl-2-(N,N-dimethyl) aminonaphthalene (PRODAN)-labelled actin with actin-binding proteins and drugs. *Biochem. J.* 290: 411-417.

The invention claimed is:

1. A functional derivative of kabiramide C wherein the 7'-hydroxyl position on the macrolide ring is modified with a methoxycoumarin or a diethylaminocoumarin group.

* * * * *